US010590165B2

(12) United States Patent
Miao et al.

(10) Patent No.: US 10,590,165 B2
(45) Date of Patent: Mar. 17, 2020

(54) ANTIBODY DRUG CONJUGATES

(71) Applicant: Sorrento Therapeutics, Inc., San Diego, CA (US)

(72) Inventors: Zhenwei Miao, San Diego, CA (US); Gang Chen, San Diego, CA (US); Tong Zhu, San Diego, CA (US); Alisher B. Khasanov, San Diego, CA (US); Dylan Deng, San Diego, CA (US); Hong Zhang, San Diego, CA (US)

(73) Assignee: Sorrento Therapeutics, Inc., San Diego, CA (US)

(*) Notice: Subject to any disclaimer, the term of this patent is extended or adjusted under 35 U.S.C. 154(b) by 326 days.

(21) Appl. No.: 15/009,775

(22) Filed: Jan. 28, 2016

(65) Prior Publication Data
US 2017/0190736 A1    Jul. 6, 2017

Related U.S. Application Data

(60) Provisional application No. 62/108,894, filed on Jan. 28, 2015.

(51) Int. Cl.
C07K 5/062    (2006.01)
A61K 47/68    (2017.01)
A61P 35/00    (2006.01)
C07K 16/32    (2006.01)

(52) U.S. Cl.
CPC ...... C07K 5/06052 (2013.01); A61K 47/6811 (2017.08); A61K 47/6813 (2017.08); A61K 47/6871 (2017.08); A61K 47/6889 (2017.08); A61P 35/00 (2018.01); C07K 16/32 (2013.01)

(58) Field of Classification Search
None
See application file for complete search history.

(56) References Cited

U.S. PATENT DOCUMENTS

| | | | |
|---|---|---|---|
| 5,780,588 A | 7/1998 | Pettit et al. | |
| 6,124,431 A | 9/2000 | Sakakibara et al. | |
| 6,569,834 B1 | 5/2003 | Pettit et al. | |
| 7,531,162 B2 | 5/2009 | Collins et al. | |
| 7,767,205 B2 | 8/2010 | Mao et al. | |
| 7,829,531 B2 | 11/2010 | Senter et al. | |
| 7,994,135 B2 | 8/2011 | Doronina et al. | |
| 8,088,387 B2 | 1/2012 | Steeves et al. | |
| 8,470,984 B2 | 6/2013 | Caruso et al. | |
| 9,884,127 B2* | 2/2018 | Miao | C07D 207/08 |
| 2005/0238649 A1 | 10/2005 | Doronina et al. | |
| 2006/0128754 A1 | 6/2006 | Hoefle et al. | |
| 2007/0134243 A1 | 6/2007 | Gazzard et al. | |
| 2011/0206658 A1 | 8/2011 | Crowley et al. | |
| 2011/0217321 A1 | 9/2011 | Torgov et al. | |
| 2011/0245295 A1 | 10/2011 | Chai et al. | |
| 2011/0263650 A1 | 10/2011 | Ellman et al. | |
| 2011/0268751 A1 | 11/2011 | Sievers et al. | |
| 2011/0301334 A1 | 12/2011 | Bhakta et al. | |
| 2012/0148610 A1 | 6/2012 | Doronina et al. | |
| 2013/0029900 A1 | 1/2013 | Widdison | |
| 2013/0101546 A1 | 4/2013 | Yurkovetskiy et al. | |
| 2013/0224228 A1 | 8/2013 | Jackson et al. | |
| 2014/0030282 A1 | 1/2014 | Polakis et al. | |
| 2015/0105539 A1 | 4/2015 | Miao et al. | |
| 2015/0105540 A1 | 4/2015 | Miao et al. | |
| 2015/0141646 A1 | 5/2015 | Miao et al. | |
| 2016/0067350 A1 | 3/2016 | Miao et al. | |

FOREIGN PATENT DOCUMENTS

| | | | |
|---|---|---|---|
| CA | 2813056 A1 | 4/2012 | |
| EP | 0624377 A2 | 11/1994 | |
| WO | 2005/081711 A2 | 9/2005 | |
| WO | 2007/109567 A1 | 9/2007 | |
| WO | 2010/009124 A2 | 1/2010 | |
| WO | 2012/010287 A1 | 1/2012 | |
| WO | 2012/166559 A1 | 12/2012 | |
| WO | 2012/166560 A1 | 12/2012 | |
| WO | 2013/173391 A1 | 11/2013 | |
| WO | 2013/173392 A1 | 11/2013 | |
| WO | 2013/173393 A1 | 11/2013 | |
| WO | 2013/185117 A1 | 12/2013 | |
| WO | 2013/192360 A1 | 12/2013 | |
| WO | 2015/057876 A1 | 4/2015 | |
| WO | 2016094455 A1 | 6/2016 | |
| WO | 2016/123412 A1 | 8/2016 | |
| WO | 2016/127081 A1 | 8/2016 | |

OTHER PUBLICATIONS

Pettit, et al., "Specific Activities of Dolastatin 10 and Peptide Derivatives Against Crypococcus neoformans" Antimicrobial Agents and Chemotherapy, Nov. 1998, p. 2961-2965.
Cella, R., et al., "Steroselective Synthesis of the Dolastatin Units by Organotriflouroborates Additions to Alpha-Amino Aldehydes", Tetrahedron Letters, 49 (2008) 16-19.
Kingston, David "Tubulin Interactive Natural Products as Anticancer Agents" J Nat Prod. Mar. 2009; 72(3): 507-515.
Younes, A. et al., "Brentuximab Vedotin (SGN-35) for Relapsed CD30-Positive Lymphomas" The New England Journal of Medicine, 363; 19, 2010, 1812-1821.
Ducry, L. et al., "Antibody-Drug Conjugates: Linking Cytotoxic Payloads to Monoclonal Antibodies" Bioconjugate Chemistry, 2010, vol. 21, No. 1, pp. 5-13.
PubChemCompound datasheet (online compound summary) CID 56841603; Create Date: Mar. 21, 2012; http://pubchem.ncbi.nlm.nih.gov/summary/summary.cgi?cid=56841603.
U.S. Appl. No. 14/401,114, filed Nov. 13, 2014.
U.S. Appl. No. 14/401,115, filed Nov. 13, 2014.

(Continued)

Primary Examiner — Patricia Duffy
(74) Attorney, Agent, or Firm — McNeill Baur PLLC

(57) ABSTRACT

There is disclosed a Dolastatin derivative, conjugated to an antibody, comprising a Dolastatin derivative moiety of Formula IV.

14 Claims, 8 Drawing Sheets

(56) References Cited

OTHER PUBLICATIONS

U.S. Appl. No. 14/401,318, filed Nov. 14, 2014.
U.S. Appl. No. 14/515,352, filed Oct. 15, 2014.
U.S. Appl. No. 15/017,174, filed Feb. 5, 2016.
Supplementary European Search Report relating to European Application No. 16744147, dated Aug. 10, 2018.

* cited by examiner

Vehicle

T-DM1, 3mg/kg

ADC 16, 3 mg/kg

ANTIBODY DRUG CONJUGATES

CROSS REFERENCE TO PRIOR APPLICATION

This patent application claims priority to U.S. provisional patent application 62/108,894 filed 28 Jan. 2015.

TECHNICAL FIELD

The present disclosure provides antibody drug conjugates (Formula I) comprising a Dolastatin derivative moiety of Formula II as the drug component.

BACKGROUND

Dolastatins, such as natural product Dolastatin 10, and its synthetic derivatives Monomethyl Auristatin E (MMAE) and Monomethyl Auristatin F (MMAF) are products that show potent antineoplastic and tubulin inhibitory property. Because of their high toxicity, the direct use of Dolastatins as therapeutic agents has not been effective. Instead, they were conjugated to an antibody for targeted delivery to kill cancer cells.

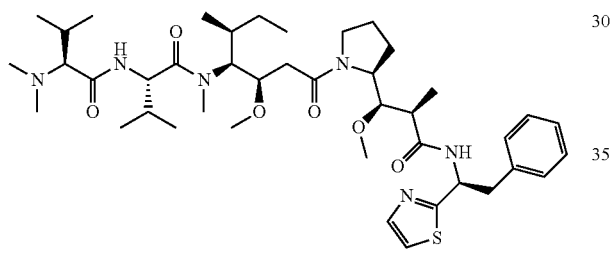

Dolastatin 10

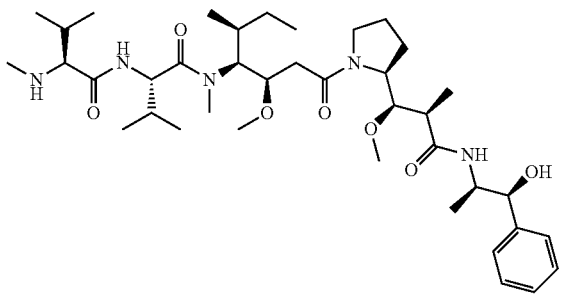

MMAE

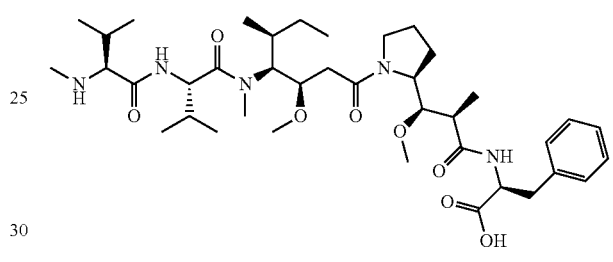

MMAF

SUMMARY

The present disclosure provides a compound comprising a Dolastatin derivative moiety of Formula IV:

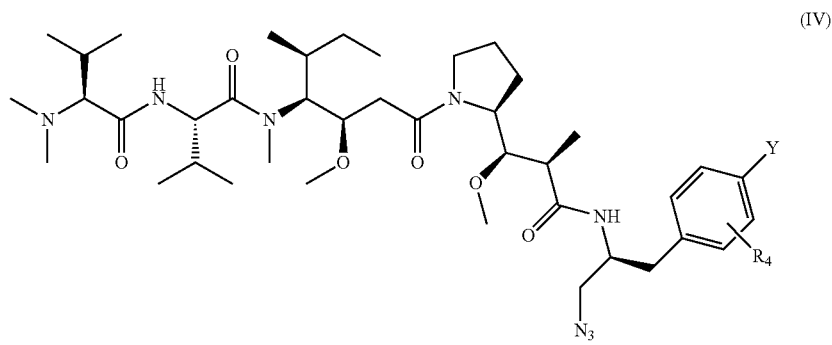

(IV)

wherein Y is OH, or NH$_2$,
R$_4$ is OH, NH$_2$, F, Cl, Br, I, OR$_5$, wherein R$_5$ is C1-C4 alkyl.

The present disclosure further provides an antibody drug-conjugate having the structure of Formula I:

 (I)

or a pharmaceutically acceptable salt thereof,
wherein:
Ab is a monoclonal antibody
L$^1$ is a connector
L$^2$ is a linker
D is an active agent having the structure of Formula II

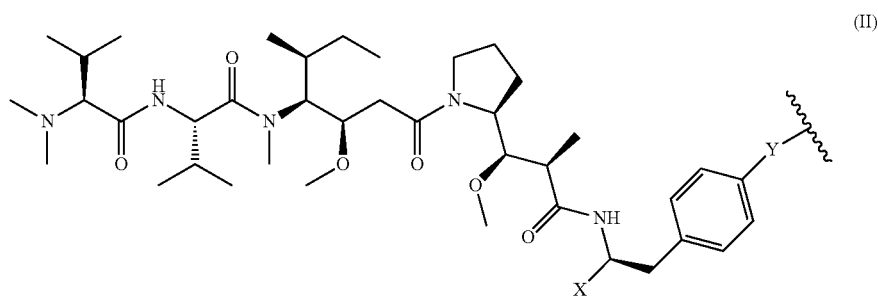

wherein Y is O, or NH, the wavy line indicates the point of attachment,
X is —CH$_2$N$_3$ or

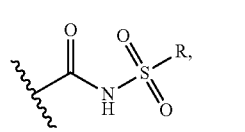

wherein R is C1-C8 alkyl, C3-C6 cyclic alkyl, aryl or heteroaryl.
n is an integer from 1-8.

Preferably, L$^2$ is selected from the group consisting of an amino acid, peptide, —(CH$_2$)$_n$—, —(CH$_2$CH$_2$O)$_n$—, p-aminobenzyl (PAB), Val-Cit (Citrulline)-PAB, Val-Ala-PAB, Ala-Ala-Asn-PAB, or combinations thereof. Preferably, -L$^1$-L$^2$ is selected from the group consisting of

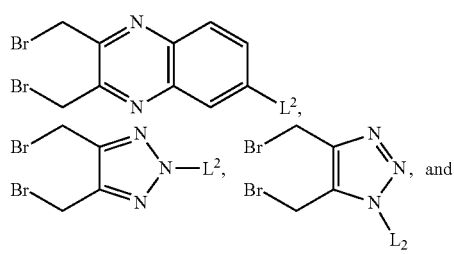

Preferably, Ab-L$^1$-L$^2$ is selected from the group consisting of

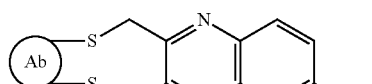

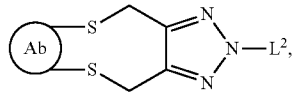

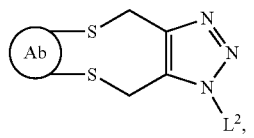

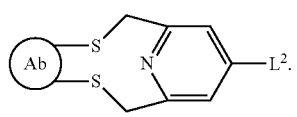

The present disclosure further provides a method for synthesizing an antibody drug-conjugate having the structure of Formula I:

 (I)

or a pharmaceutically acceptable salt thereof,
wherein:
Ab is a monoclonal antibody
L$^1$ is a connector
L$^2$ is a linker D is an active agent having the structure of Formula II

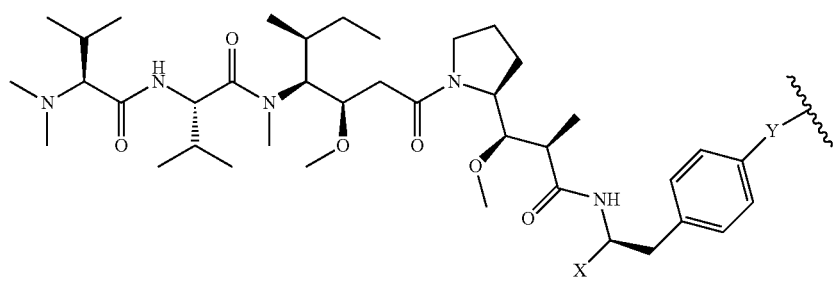

(II)

wherein Y=O, or NH, the wavy line indicates the point of attachment
X is —CH₂N₃ or

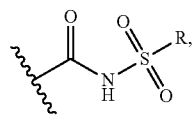

wherein R is C1-C8 alkyl, C3-C6 cyclic alkyl, aryl or heteroaryl.
n is an integer from 1-8, comprising
reacting a compound of formula III with a Lys on an Ab

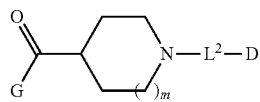

III wherein G is selected from the group consisting of —F, —Cl, —Br, —I, —N₃, —OR, SR, —ONRR, RC(=O)O—, and RSO₂—O—; and
R is optionally substituted alkyl, or optionally substituted aryl.
m=0, or 1.

DETAILED DESCRIPTION

Figure 1:
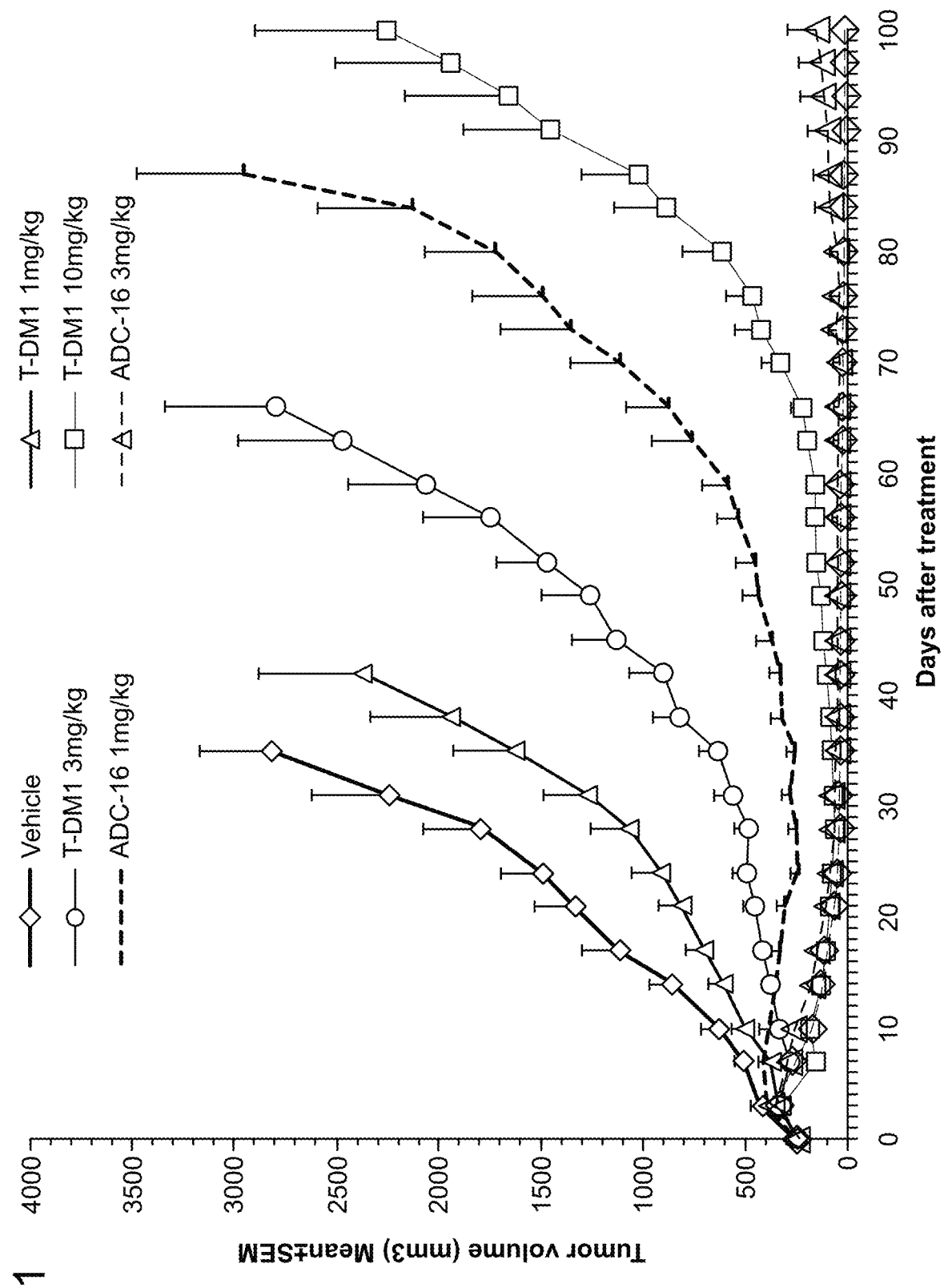
FIG. 1 shows a single dose of conjugate 16 administered to BALB/c nude mice (n=8) by intravenous administration.

The present disclosure provides compounds and conjugates, such as ADC (antibody drug conjugates), wherein a linker moiety that is peptide based has an attaching point at its C terminal which reacts with either Cys or Lys on an antibody in a controlled fashion. For Lys conjugation, for example, the DAR (drug antibody ratio) is 2. The DAR (drug antibody ratio) of the majority of conjugate is 4, when conjugation occurred on Cys.

TABLE 1

Examples of structures of drug-linker moieties for Lys conjugation onto an antibody.

| Compound ID | Structures |
|---|---|
| 1 | 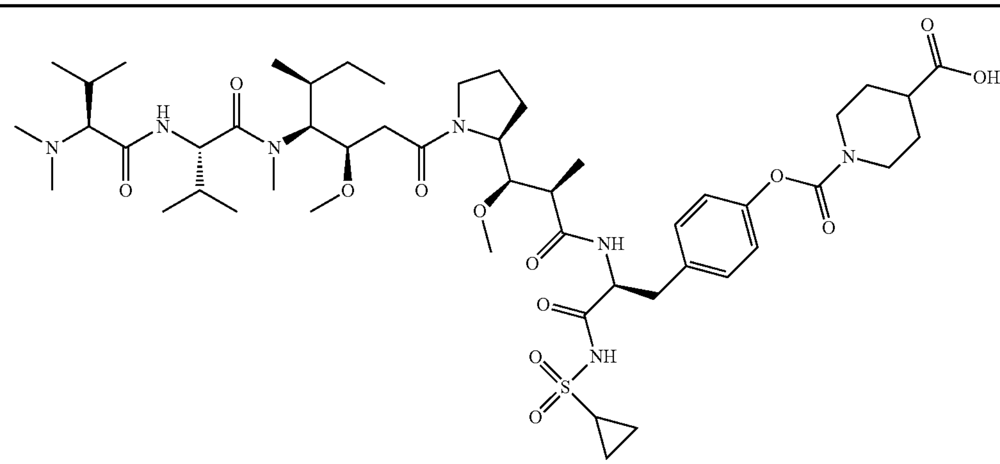 |

TABLE 1-continued
Examples of structures of drug-linker moieties for Lys conjugation onto an antibody.
| Compound ID | Structures |
|---|---|
| 2 | 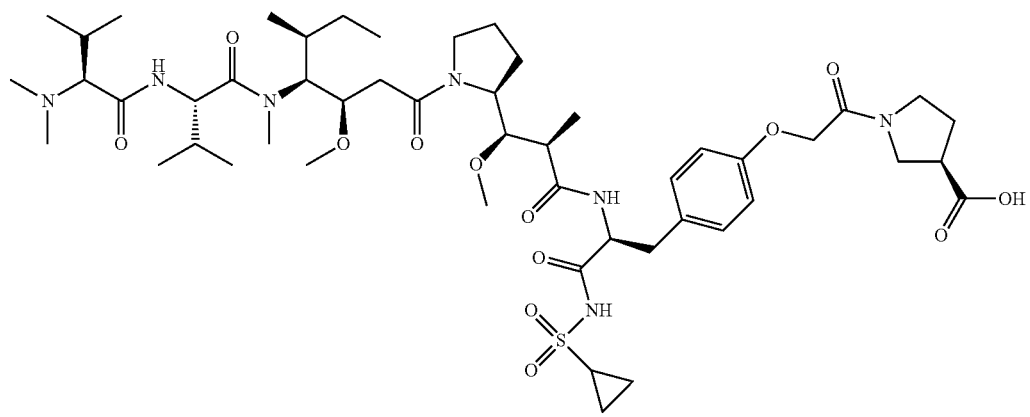 [SMILES: CC[C@H](C)[C@@H]([C@@H](CC(=O)N1CCC[C@H]1[C@H](OC)[C@@H](C)C(=O)N[C@@H](Cc1ccc(OCC(=O)N2CC[C@@H](C(=O)O)C2)cc1)C(=O)NS(=O)(=O)C1CC1)OC)N(C)C(=O)[C@@H](NC(=O)[C@H](C(C)C)N(C)C)C(C)C] |
| 4 | 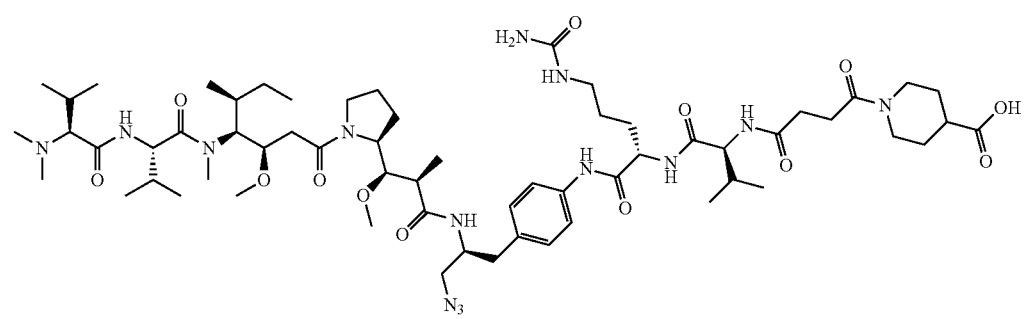 [SMILES: CC[C@H](C)[C@@H]([C@@H](CC(=O)N1CCC[C@H]1[C@H](OC)[C@@H](C)C(=O)N[C@H](CN=[N+]=[N-])Cc1ccc(NC(=O)[C@H](CCCNC(N)=O)NC(=O)[C@@H](NC(=O)CCC(=O)N2CCC(C(=O)O)CC2)C(C)C)cc1)OC)N(C)C(=O)[C@@H](NC(=O)[C@H](C(C)C)N(C)C)C(C)C] |
| 62 | 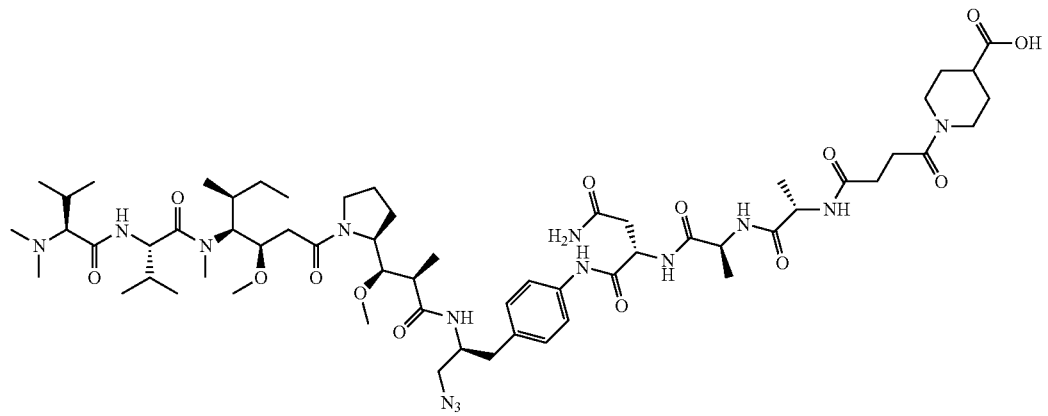 [SMILES: CC[C@H](C)[C@@H]([C@@H](CC(=O)N1CCC[C@H]1[C@H](OC)[C@@H](C)C(=O)N[C@H](CN=[N+]=[N-])Cc1ccc(NC(=O)[C@H](CC(N)=O)NC(=O)[C@H](C)NC(=O)[C@H](C)NC(=O)CCC(=O)N2CCC(C(=O)O)CC2)cc1)OC)N(C)C(=O)[C@@H](NC(=O)[C@H](C(C)C)N(C)C)C(C)C] |

TABLE 2

Examples of structures of drug-linker compounds (for Cys conjugation) to be conjugated onto a hinge region of an IgG class antibody.

| Compound ID | Structures |
|---|---|
| 6 | 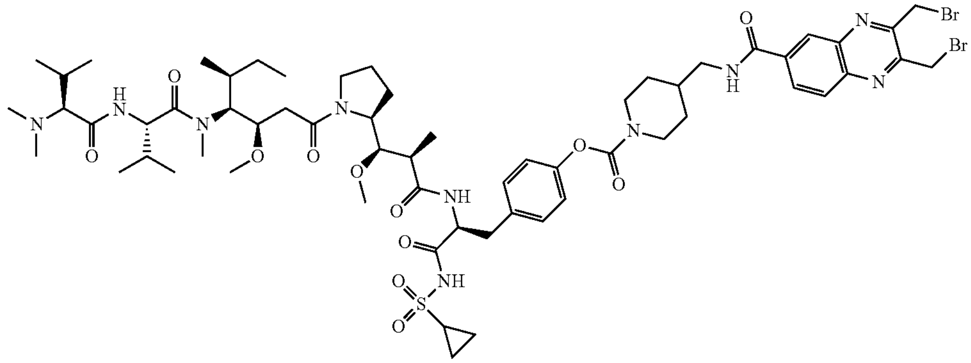 [SMILES: CC[C@H](C)[C@@H]([C@@H](CC(=O)N1CCC[C@H]1[C@H](OC)[C@@H](C)C(=O)N[C@@H](Cc1ccc(OC(=O)N2CCC(CNC(=O)c3ccc4nc(CBr)c(CBr)nc4c3)CC2)cc1)C(=O)NS(=O)(=O)C1CC1)OC)N(C)C(=O)[C@@H](NC(=O)[C@H](C(C)C)N(C)C)C(C)C] |
| 7 | 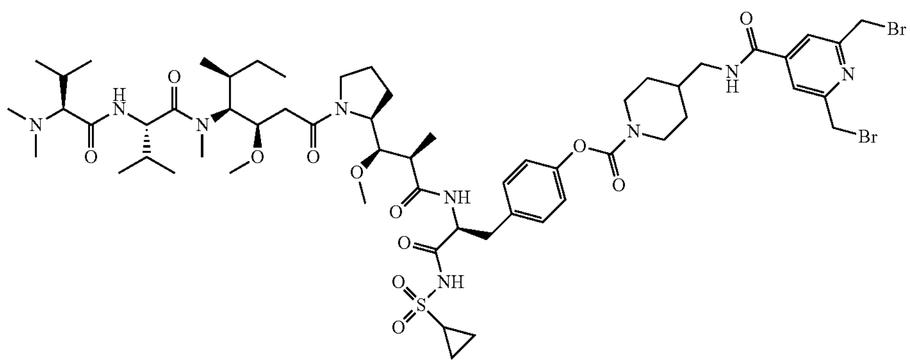 [SMILES: CC[C@H](C)[C@@H]([C@@H](CC(=O)N1CCC[C@H]1[C@H](OC)[C@@H](C)C(=O)N[C@@H](Cc1ccc(OC(=O)N2CCC(CNC(=O)c3cc(CBr)nc(CBr)c3)CC2)cc1)C(=O)NS(=O)(=O)C1CC1)OC)N(C)C(=O)[C@@H](NC(=O)[C@H](C(C)C)N(C)C)C(C)C] |
| 8 | 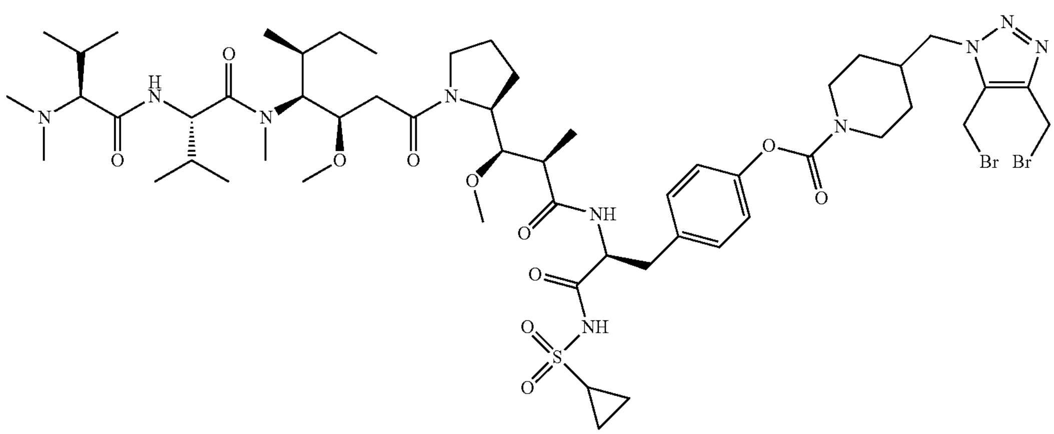 [SMILES: CC[C@H](C)[C@@H]([C@@H](CC(=O)N1CCC[C@H]1[C@H](OC)[C@@H](C)C(=O)N[C@@H](Cc1ccc(OC(=O)N2CCC(Cn3nnc(CBr)c3CBr)CC2)cc1)C(=O)NS(=O)(=O)C1CC1)OC)N(C)C(=O)[C@@H](NC(=O)[C@H](C(C)C)N(C)C)C(C)C] |
| 9 | 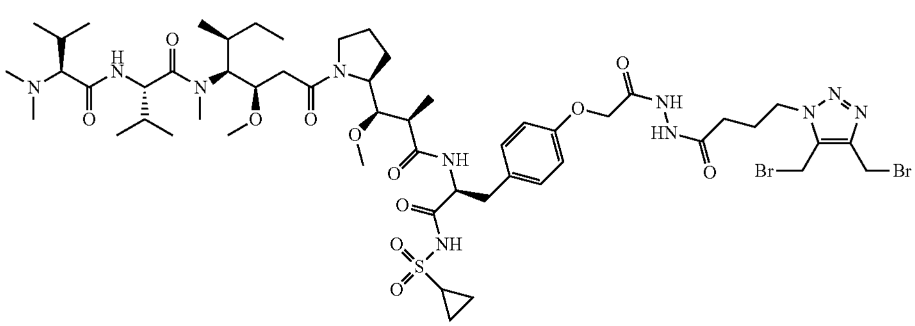 [SMILES: CC[C@H](C)[C@@H]([C@@H](CC(=O)N1CCC[C@H]1[C@H](OC)[C@@H](C)C(=O)N[C@@H](Cc1ccc(OCC(=O)NNC(=O)CCCn2nnc(CBr)c2CBr)cc1)C(=O)NS(=O)(=O)C1CC1)OC)N(C)C(=O)[C@@H](NC(=O)[C@H](C(C)C)N(C)C)C(C)C] |

TABLE 2-continued
Examples of structures of drug-linker compounds (for Cys conjugation) to be conjugated onto a hinge region of an IgG class antibody.
| Compound ID | Structures |
|---|---|
| 13 | 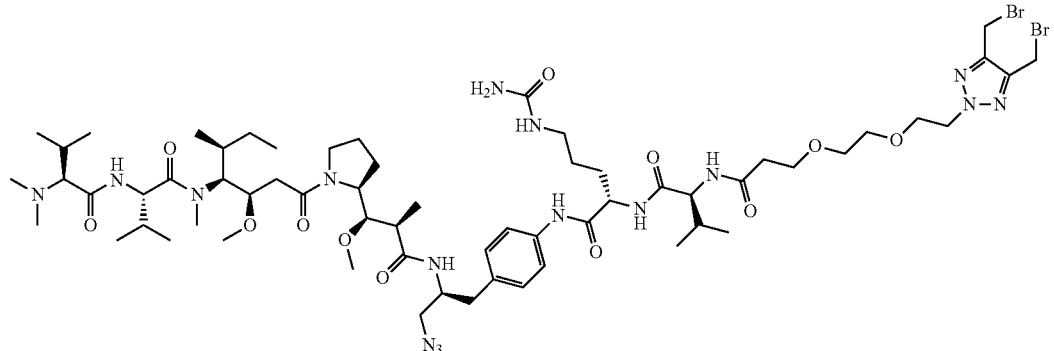 [SMILES: CC[C@H](C)[C@@H]([C@@H](CC(=O)N1CCC[C@H]1[C@H](OC)[C@@H](C)C(=O)N[C@H](CN=[N+]=[N-])Cc1ccc(NC(=O)[C@H](CCCNC(N)=O)NC(=O)[C@@H](NC(=O)CCOCCOCCn2nc(CBr)c(CBr)n2)C(C)C)cc1)OC)N(C)C(=O)[C@@H](NC(=O)[C@H](C(C)C)N(C)C)C(C)C] |
| 63 | 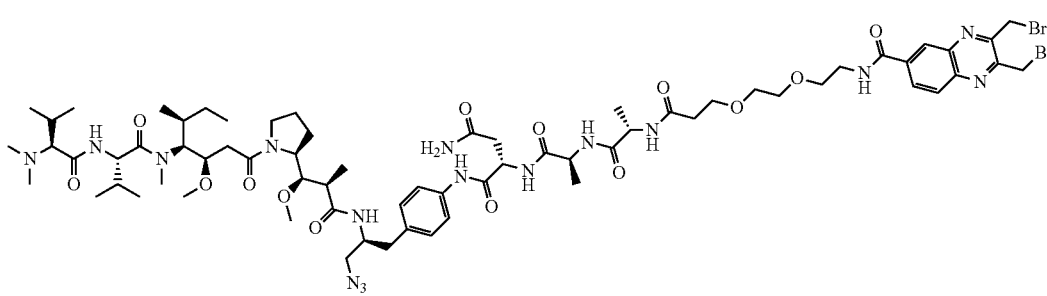 [SMILES: CC[C@H](C)[C@@H]([C@@H](CC(=O)N1CCC[C@H]1[C@H](OC)[C@@H](C)C(=O)N[C@H](CN=[N+]=[N-])Cc1ccc(NC(=O)[C@H](CC(N)=O)NC(=O)[C@H](C)NC(=O)[C@H](C)NC(=O)CCOCCOCCNC(=O)c2ccc3nc(CBr)c(CBr)nc3c2)cc1)OC)N(C)C(=O)[C@@H](NC(=O)[C@H](C(C)C)N(C)C)C(C)C] |
TABLE 3
Examples of structures of antibody (Ab)-drug conjugates.
| Compound ID | Structures |
|---|---|
| 16 | 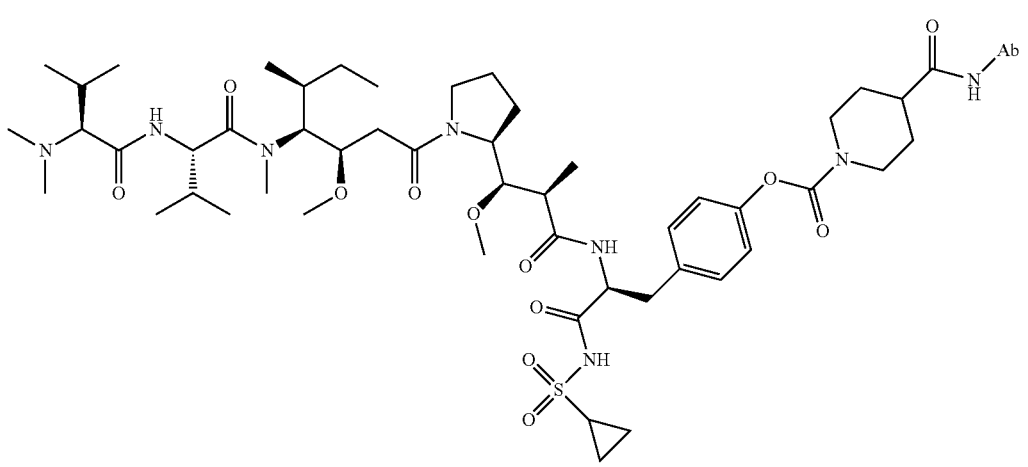 |

TABLE 3-continued

Examples of structures of antibody (Ab)-drug conjugates.

| Compound ID | Structures |
| --- | --- |
| 17 | 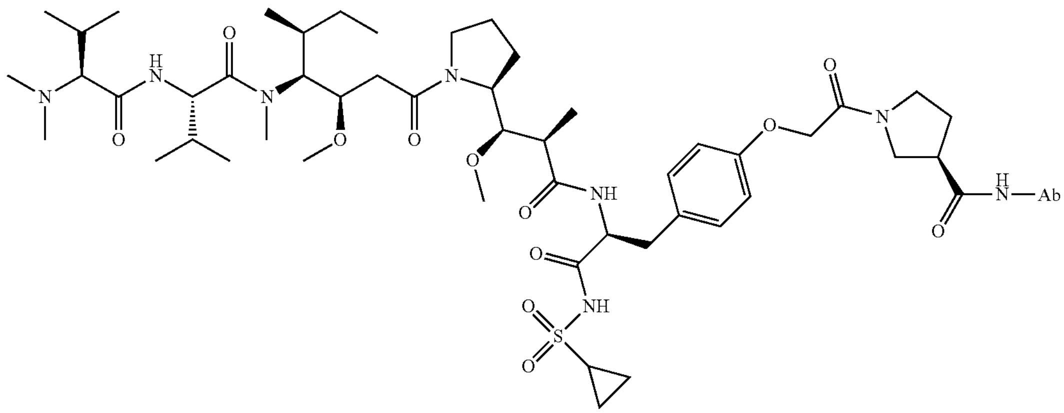 |
| 19 | 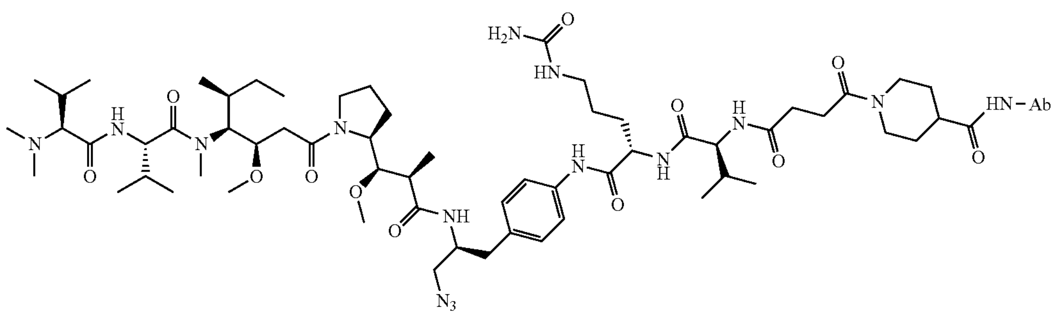 |
| 64 | 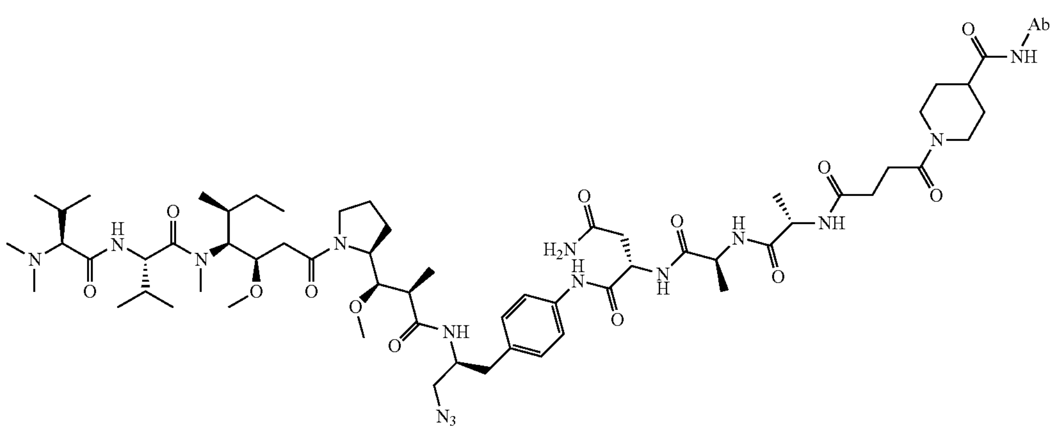 |
| 21 | 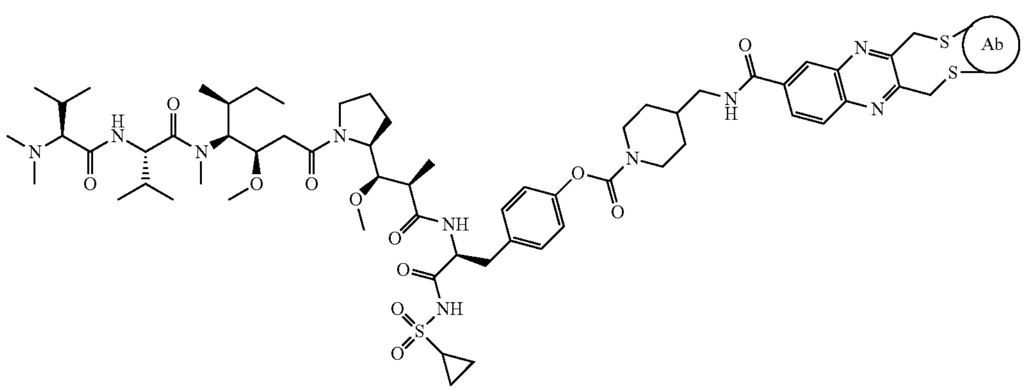 |

TABLE 3-continued

Examples of structures of antibody (Ab)-drug conjugates.

| Compound ID | Structures |
| --- | --- |
| 22 | 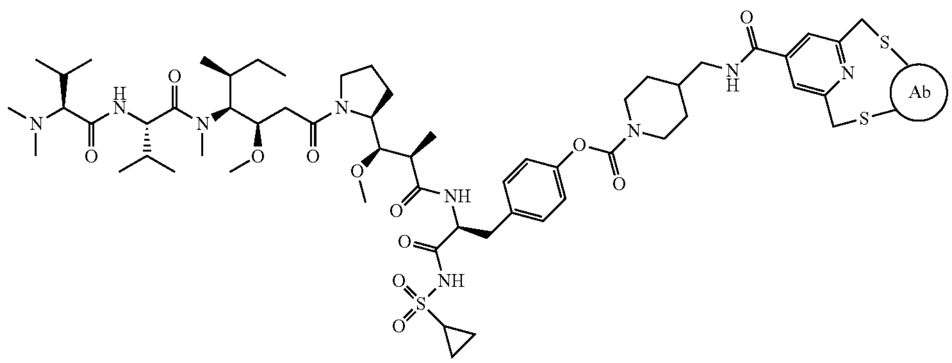 |
| 23 | 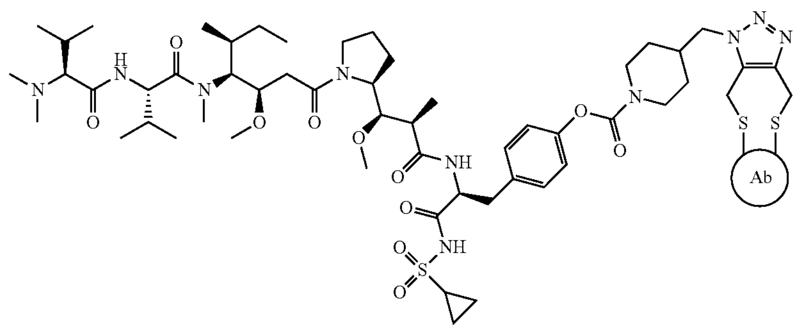 [SMILES: CC[C@H](C)[C@@H]([C@@H](CC(=O)N1CCC[C@H]1[C@H](OC)[C@@H](C)C(=O)N[C@@H](Cc1ccc(OC(=O)N2CCC(Cn3nnc(CSC)c3CSC)CC2)cc1)C(=O)NS(=O)(=O)C1CC1)OC)N(C)C(=O)[C@@H](NC(=O)[C@H](C(C)C)N(C)C)C(C)C] |
| 24 | 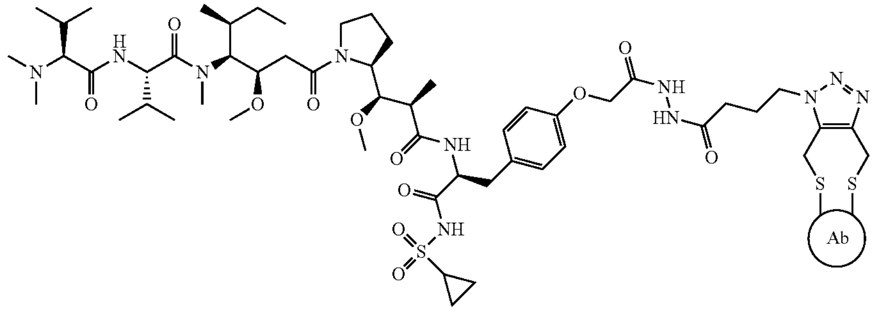 [SMILES: CC[C@H](C)[C@@H]([C@@H](CC(=O)N1CCC[C@H]1[C@H](OC)[C@@H](C)C(=O)N[C@@H](Cc1ccc(OCC(=O)NNC(=O)CCCn2nnc(CSC)c2CSC)cc1)C(=O)NS(=O)(=O)C1CC1)OC)N(C)C(=O)[C@@H](NC(=O)[C@H](C(C)C)N(C)C)C(C)C] |
| 28 | 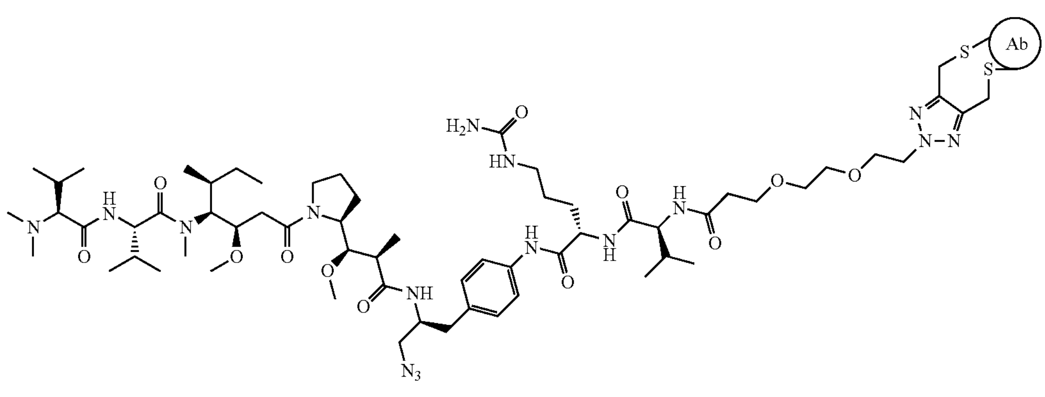 |

TABLE 3-continued

Examples of structures of antibody (Ab)-drug conjugates.

| Compound ID | Structures |
|---|---|
| 65 | 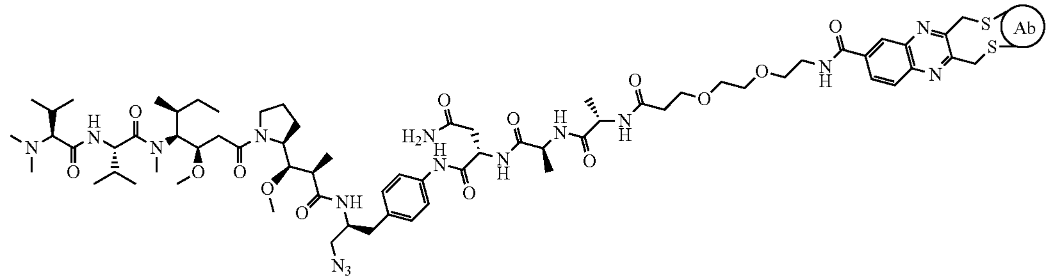 |

Definitions

Abbreviations are defined as follows:
Ac Acetyl
aq. Aqueous
BOC or Boc tert-Butoxycarbonyl
BrOP bromo tris(dimethylamino) phosphonium hexafluorophosphate
Bu n-Butyl
° C. Temperature in degrees Centigrade
Cit Citrulline
DCM methylene chloride
DEPC Diethylcyanophosphonate
DIC diisopropylcarbodiimide
DIEA Diisopropylethylamine
DMA N,N'-Dimethylacetamide
DMF N,N'-Dimethylformamide
EDC 1-Ethyl-3-(3-dimethylaminopropyl)carbodiimide
Et Ethyl
EtOAc Ethyl acetate
Eq Equivalents
Fmoc 9-Fluorenylmethoxycarbonyl
g Gram(s)
h Hour (hours)
HATU 2-(1H-7-azabenzotriazol-1-yl)-1,1,3,3-tetramethyl uronium hexafluorophosphate
HOBT N-Hydroxybenzotriazole
HOSu N-Hydroxysuccinimide
HPLC High-performance liquid chromatography
LC/MS Liquid chromatography-mass spectrometry
Me Methyl
MeOH Methanol
MeCN Acetonitrile
mL Milliliter(s)
MS mass spectrometry
PAB p-aminobenzyl
RP-HPLC reverse phase HPLC
rt room temperature
t-Bu tert-Butyl
TEA Triethylamine
Tert, t tertiary
TFA Trifluoroacetic acid
THF Tetrahydrofuran
TLC Thin-layer chromatography
μL Microliter(s)

General Synthesis Procedure—Formation of an Activated Ester (e.g. NHS) from an Acid An acid was dissolved in DCM (methylene chloride) and DMF (N,N' dimethyl formamide) was added to aid dissolution if necessary. N-hydroxysuccinimide (1.5 eq) was added, followed by EDC.HCl (1-Ethyl-3-(3-dimethylaminopropyl)carbodiimide) (1.5 eq). The reaction mixture was stirred at room temperature for 1 h until most of the acid was consumed. The progress of the reaction was monitored by RP-HPLC. The mixture was then diluted with DCM and washed successively with citric acid (aq. 10%) and brine. The organic layer was dried and concentrated to dryness. The crude product was optionally purified by RP-HPLC or silica gel column chromatography.

Example 1

Preparation of Compound 1

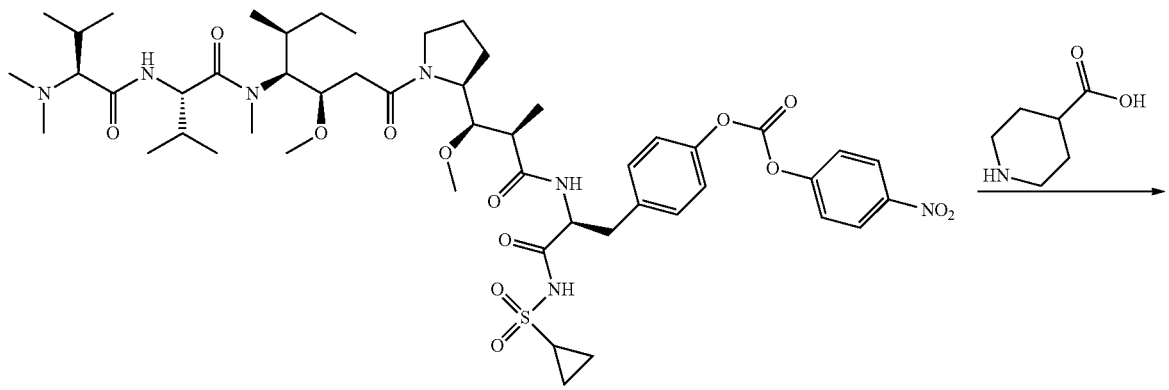

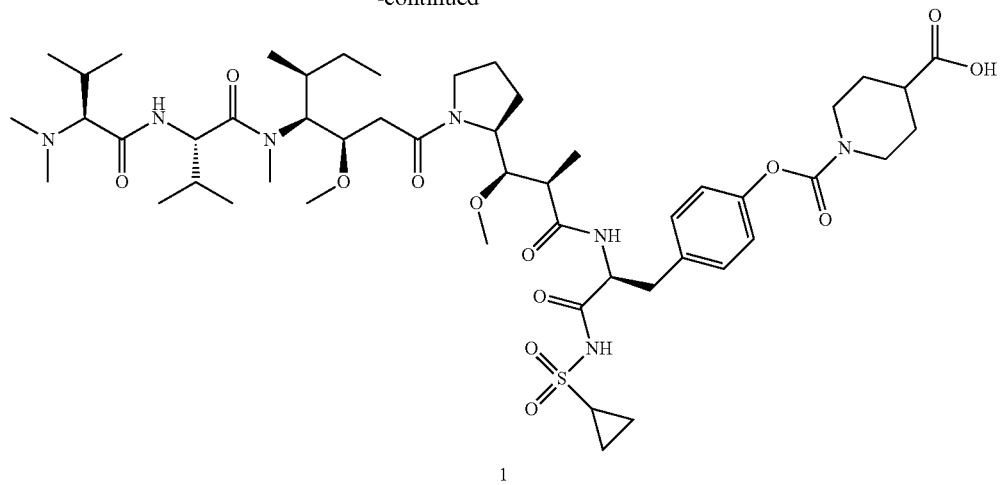

1

To a crude solution of compound 47 (0.1 mmol) in THF (3 mL) was added a solution of piperidine 4-carboxylic acid (60 mg) in sat. aq. NaHCO₃ (1 mL). The mixture was stirred at room temperature for 30 min, then acidified with 1N aq. HCl to pH=4-5. The reaction mixture was concentrated and the residue was purified by reverse phase HPLC to give compound 1 as a white powder after lyophilization (68 mg). MS m/z 1020.7 (M+H).

Example 2

Preparation of Compound 2

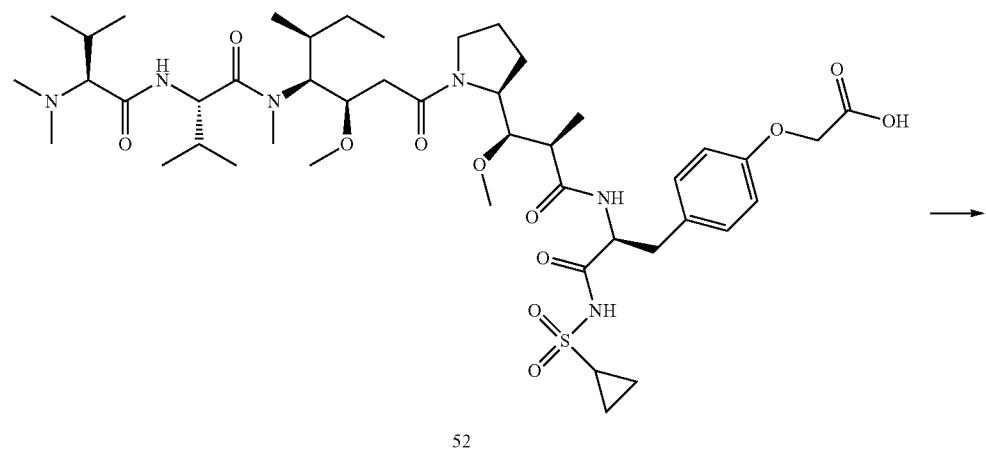

52

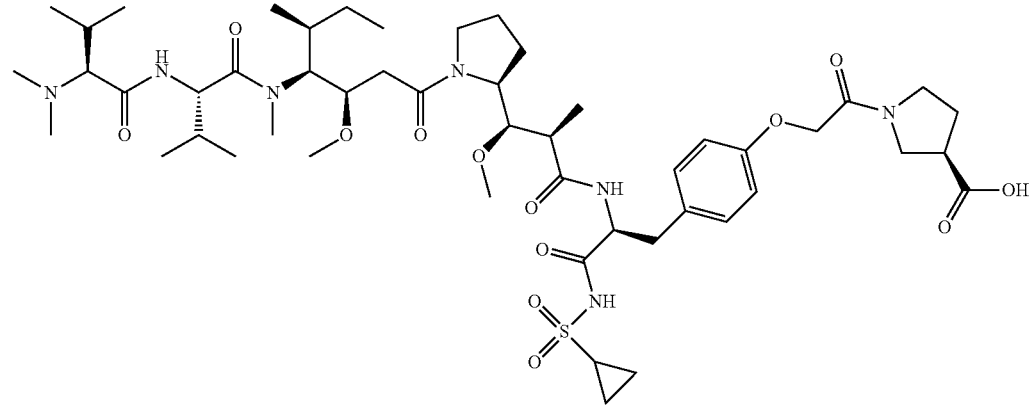

2

Compound 52 (185 mg, 0.2 mmol) was dissolved in DCM/DMF (5/1, v/v, 5 mL).

EDC.HCl (0.5 mmol) and HOSu (0.3 mmol) were added. The mixture was stirred at room temperature for 30 min. HPLC analysis confirmed that all of compound 52 was consumed. The reaction was diluted with DCM (50 mL) and washed with brine. The organic layer was concentrated to 1 mL and diluted with acetonitrile/water (6/4, v/v, 3 mL). A solution of pyrrolidine 3-carboxylic acid (60 mg) in sat. aq. NaHCO$_3$ (1 mL) was added and the mixture was stirred at room temperature for 10 min. The reaction was acidified with HOAc and concentrated. The crude product was purified by RP-HPLC to give compound 2 (138 mg, 68%). MS m/z 1020.6 (M+H).

Example 3

Preparation of Compound 4

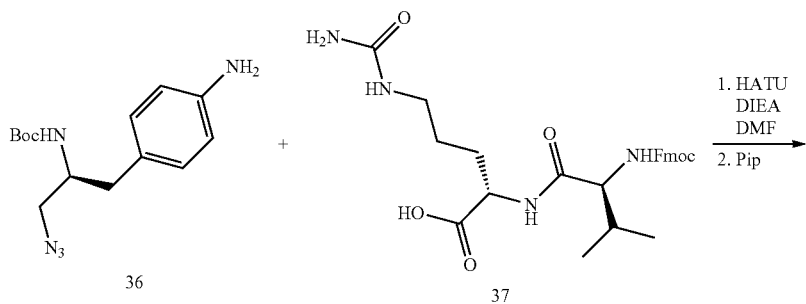

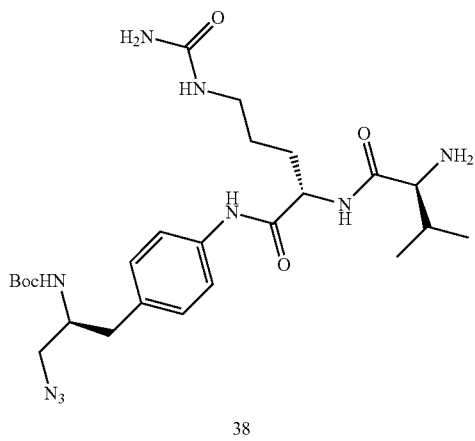

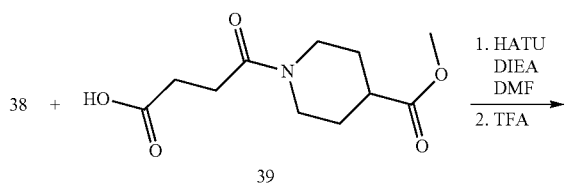

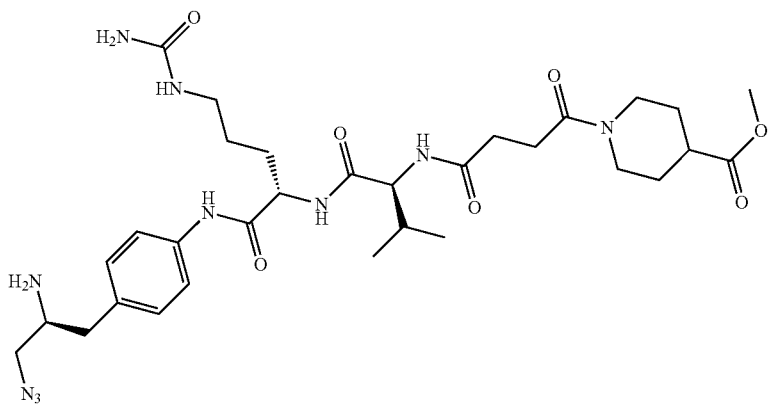

-continued

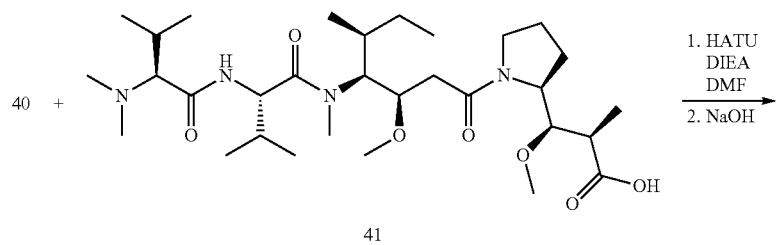

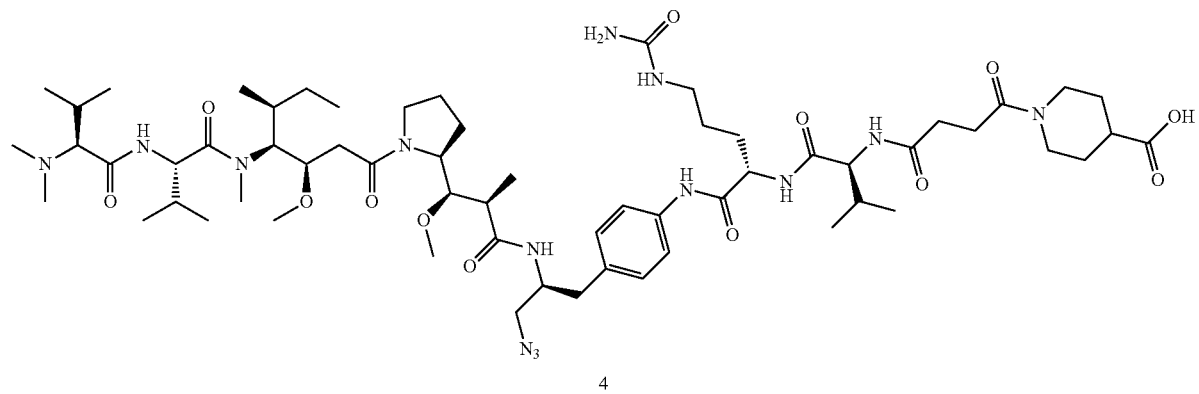 [SMILES: CC[C@H](C)[C@@H]([C@@H](CC(=O)N1CCC[C@H]1[C@H](OC)[C@@H](C)C(=O)N[C@H](CN=[N+]=[N-])Cc1ccc(NC(=O)[C@H](CCCNC(N)=O)NC(=O)[C@@H](NC(=O)CCC(=O)N2CCC(C(=O)O)CC2)C(C)C)cc1)OC)N(C)C(=O)[C@@H](NC(=O)[C@H](C(C)C)N(C)C)C(C)C]

Preparation of Compound 38:

To compound 37 (261 mg, 0.52 mmol) in 6 mL of DMF was added HATU (217 mg, 0.57 mmol), DIEA (362 μL, 2.08 mmol), and amine 36 (213 mg, 0.52 mmol). The mixture was stirred for 30 min, then 400 μL of piperidine was added and stirred for 10 min. The mixture was evaporated and purified by HPLC to give compound 38 (171 mg, 60%). MS m/z 548.3 (M+H).

Preparation of Compound 40:

To compound 39 (37 mg, 0.15 mmol) in 4 mL of DMF was added HATU (59 mg, 0.15 mmol), DIEA (108 μL, 0.6 mmol), and amine 38 (102 mg, 0.15 mmol). The mixture was stirred for 30 min, then evaporated to dryness. The residue was dissolved in 2 mL of DCM, then 1 mL of TFA was added and stirred for 10 min. The mixture was evaporated and purified by HPLC to give compound 40 (94 mg, 78%). MS m/z 673.4 (M+H).

Preparation of Compound 4:

To compound 41 (85 mg, 0.12 mmol) in 2 mL of DMF was added HATU (48 mg, 0.12 mmol), DIEA (83 μL, 0.48 mmol), and amine 40 (94 mg, 0.12 mmol). The mixture was stirred for 30 min, then a solution of 90 mg of NaOH in 1 mL of water was added and stirred for 30 min. The mixture purified by HPLC to give compound 4 (86 mg, 58%). MS m/z 1239.7 (M+H).

Example 4

Preparation of Compound 6

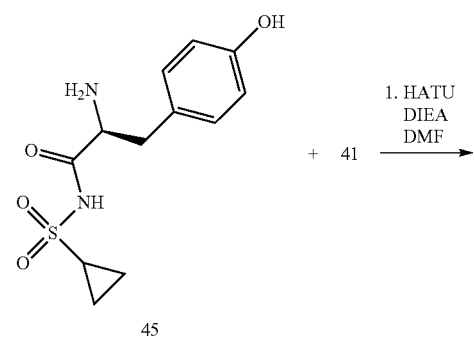

-continued
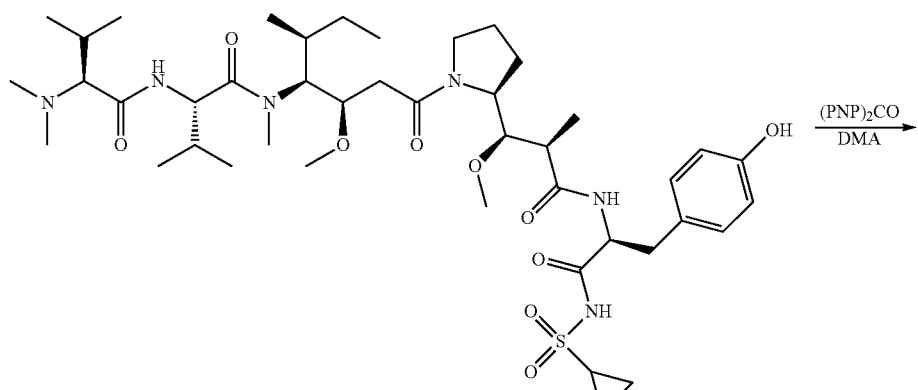
46
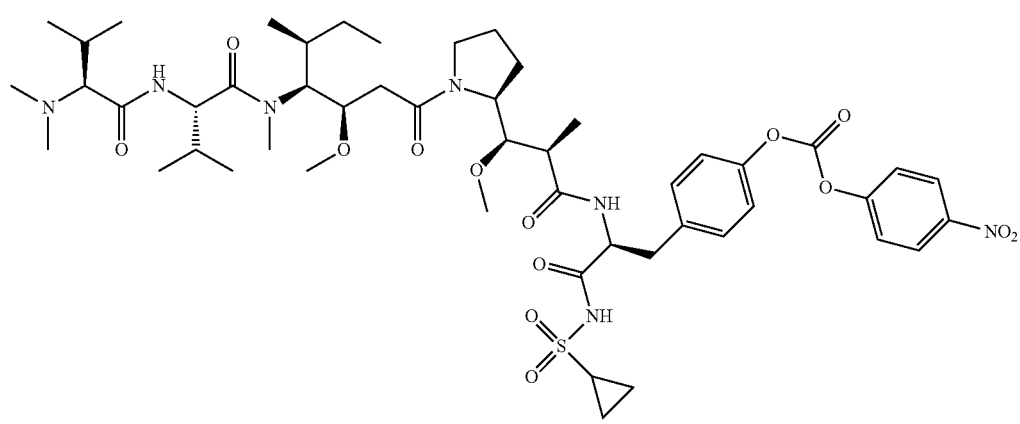
47
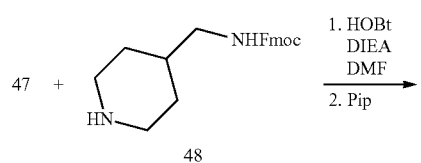
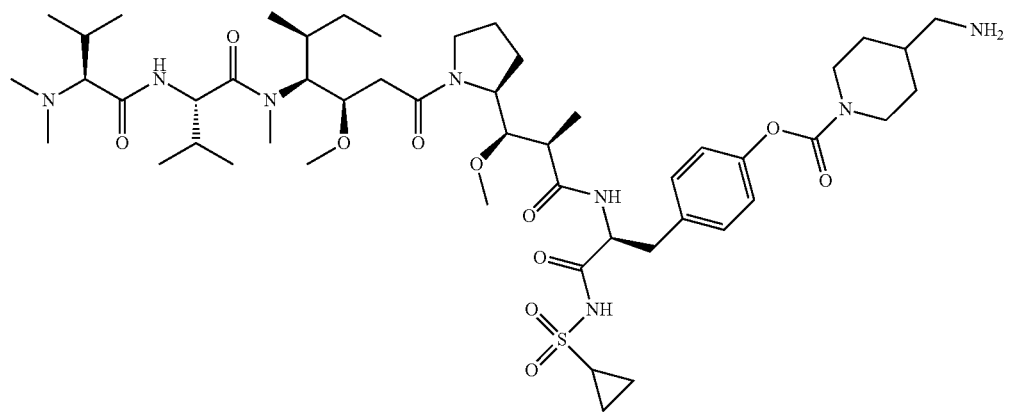
49

-continued

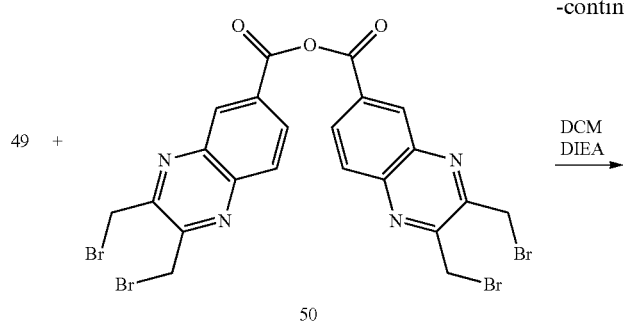

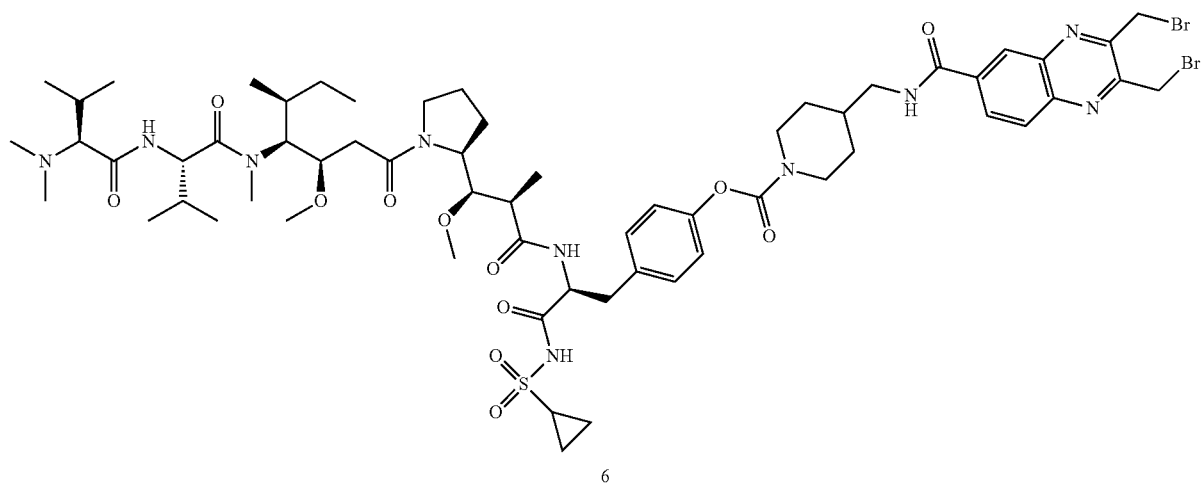

Preparation of Compound 46:

To compound 41 (1000 mg, 1.67 mmol) in 20 mL of DMF was added HATU (640 mg, 1.68 mmol), DIEA (870 μL, 5.00 mmol), and amine 45 (535 mg, 1.67 mmol). The mixture was stirred for 30 min, then evaporated and purified by HPLC to give compound 46 (1140 mg, 70%). MS m/z 865.5 (M+H).

Preparation of Compound 47:

To compound 46 (500 mg, 0.57 mmol) in 10 mL of DMA was added bis(p-nitrophenyl)carbonate (210 mg, 0.69 mmol), and DIEA (35 μL, 0.2 mmol). The mixture was stirred for 18 h, then 100 mL of ether was added and the precipitate was collected by filtration to give compound 47 (500 mg, 85%). MS m/z 1030.6 (M+H).

Preparation of Compound 49:

To compound 47 (125 mg, 0.12 mmol) in 4 mL of DMF was added HOBt (7 mg, 0.05 mmol), DIEA (21 μL, 0.12 mmol), and amine 48 (40 mg, 0.12 mmol). The mixture was stirred for 16 h, then 200 μL of piperidine was added and stirred for 10 min. The mixture was evaporated and purified by HPLC to give compound 49 (72 mg, 60%). MS m/z 1005.6 (M+H).

Preparation of Compound 6:

To compound 49 (30 mg, 0.027 mmol) in 2 mL of DCM was added DIEA (15 μL, 0.086 mmol), DIEA (50 μL, 0.288 mmol), and anhydride 50 (19 mg, 0.027 mmol). The mixture was stirred for 30 min, then evaporated and purified by HPLC to give compound 6 (32 mg, 88%). MS m/z 1347.5 (M+H).

Example 5

Preparation of Compound 7.

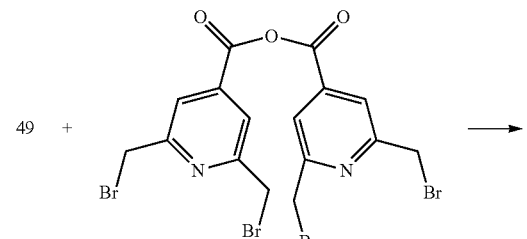

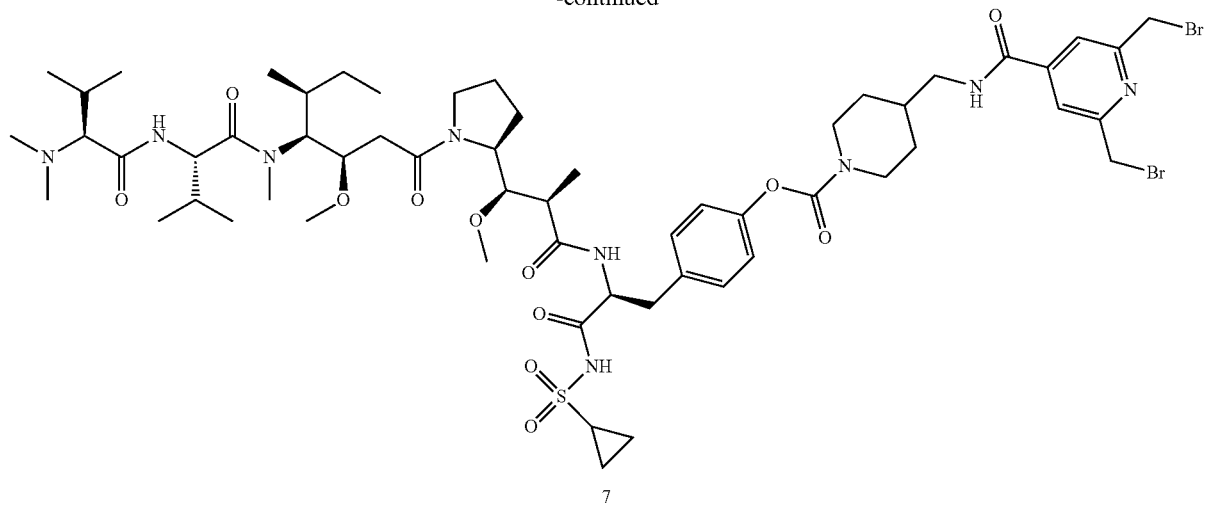
Compound 7 was synthesized from compound 49 (0.1 mmol) and anhydride 63 (0.1 mmol) as described for the synthesis of compound 6. Yield: 79%. MS m/z 1296.8 (M+H).
Example 6
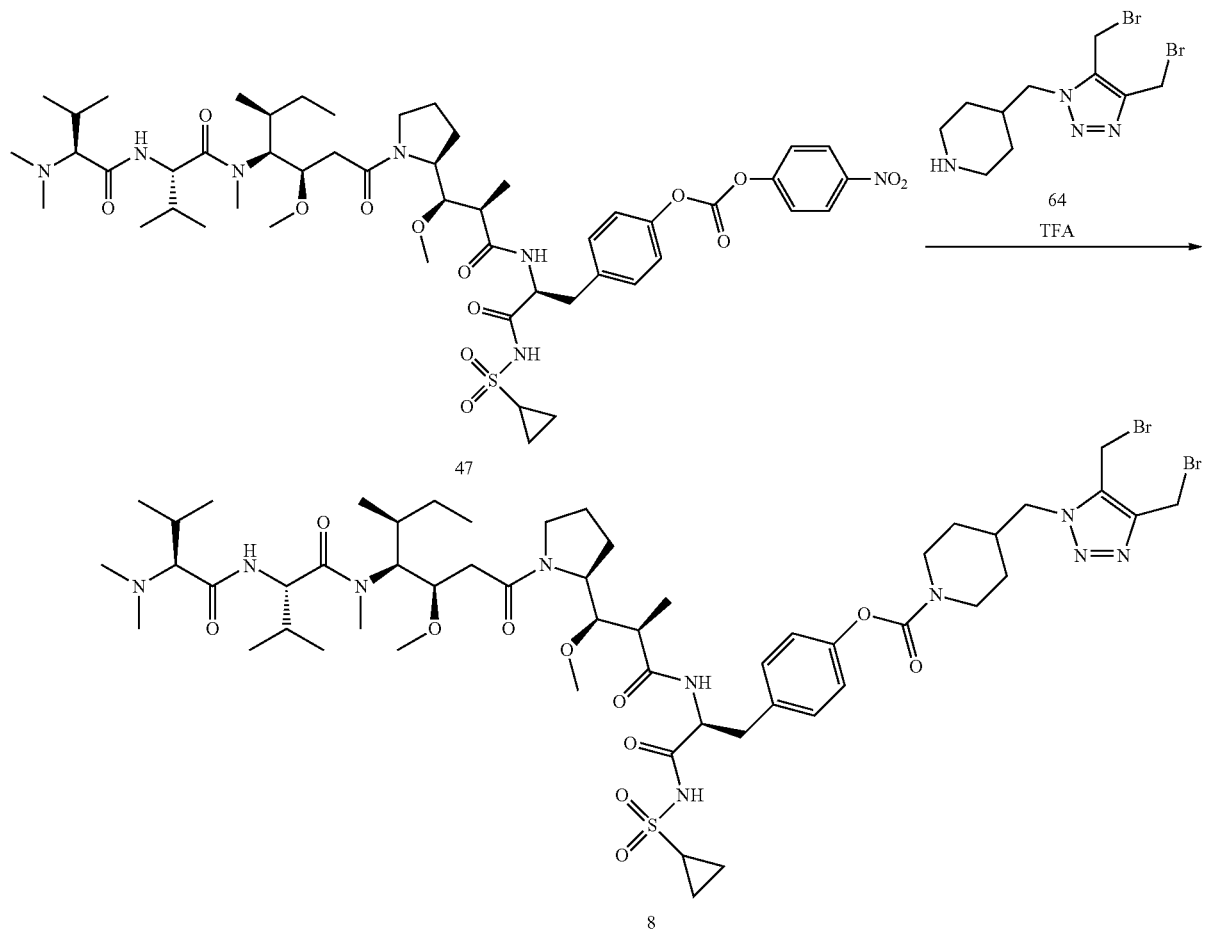

Preparation of Compound 8.
To a solution of compound 47 (0.1 mmol) in THF (3 mL) was added a solution of compound 64 (0.15 mmol, 67 mg) in acetonitrile/water (1/1, v/v, 1 mL), followed by DIEA (50 µL). After 30 min, the reaction was acidified and concentrated. The residue was purified by reverse phase HPLC to give compound 8 as a white solid (87 mg). MS m/z 1243.6 [M+H]+.
Example 7
Preparation of Compound 9.
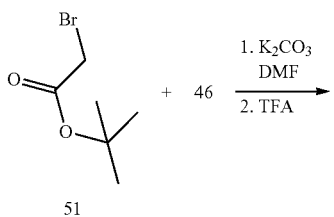
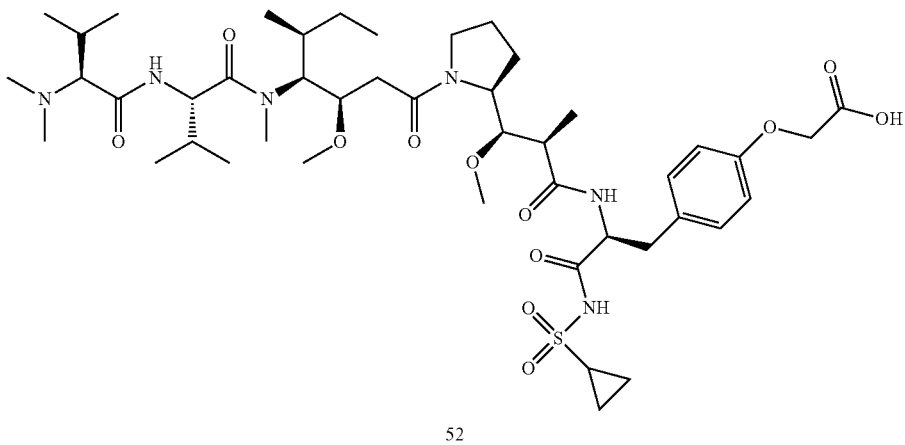
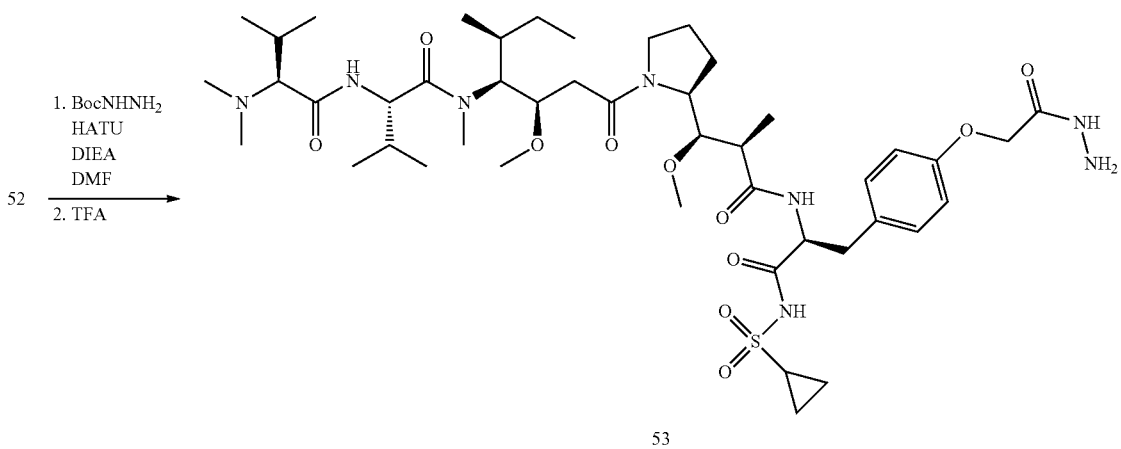
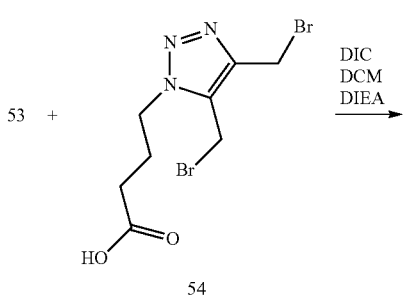

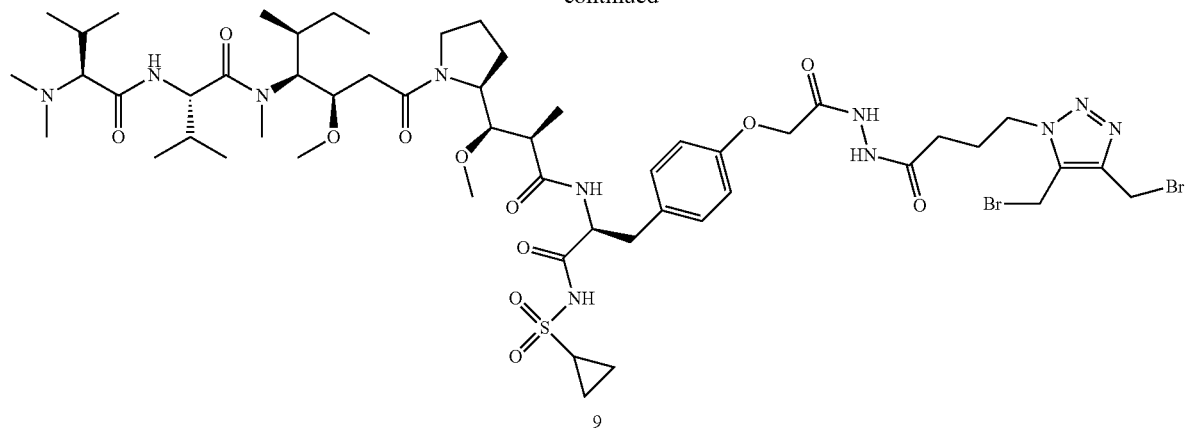

9

Preparation of Compound 52:

To compound 46 (120 mg, 0.12 mmol) in 3 mL of DMF was added $K_2CO_3$ (118 mg, 0.85 mmol), and bromoacetate 51 (35 mg, 0.18 mmol). The mixture was stirred for 16 h, then evaporated. The residue was dissolved in 2 mL of DCM, filtered, and 2 mL of TFA was added. After 20 min the mixture was evaporated and purified by HPLC to give compound 52 (92 mg, 83%). MS m/z 923.5 (M+H).

Preparation of Compound 53:

To compound 52 (92 mg, 0.1 mmol) in 2 mL of DMF was added HATU (38 mg, 0.1 mmol), DIEA (70 µL, 0.4 mmol), and boc-hydrazine (15 mg, 0.12 mmol). The mixture was stirred for 30 min, then evaporated to dryness. The residue was dissolved in 2 mL of DCM, then 1 mL of TFA was added and stirred for 10 min. The mixture was evaporated and purified by HPLC to give compound 53 (82 mg, 78%). MS m/z 937.5 (M+H).

Preparation of Compound 9:

To compound 54 (53 mg, 0.156 mmol) in 2 mL of DCM was added DIC (10 mg, 0.078 mmol) and stirred for 10 min. Then DIEA (54 µL, 0.312 mmol) and amine 53 (82 mg, 0.078 mmol) was added and the mixture was stirred for 15 min. The mixture was evaporated and purified by HPLC to give compound 9 (62 mg, 63%). MS m/z 1260.5 (M+H).

Example 8

Preparation of Compound 13

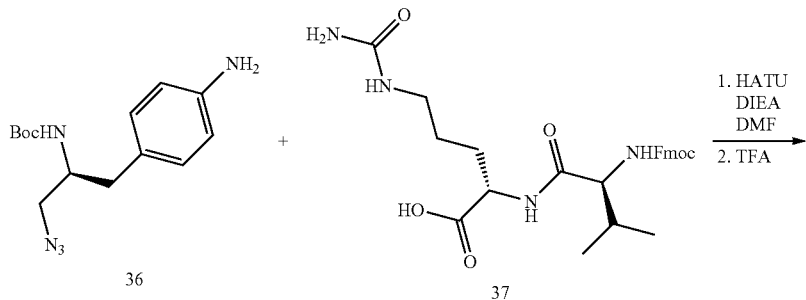

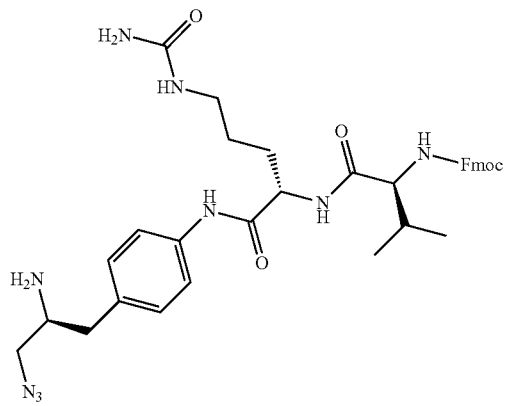

66

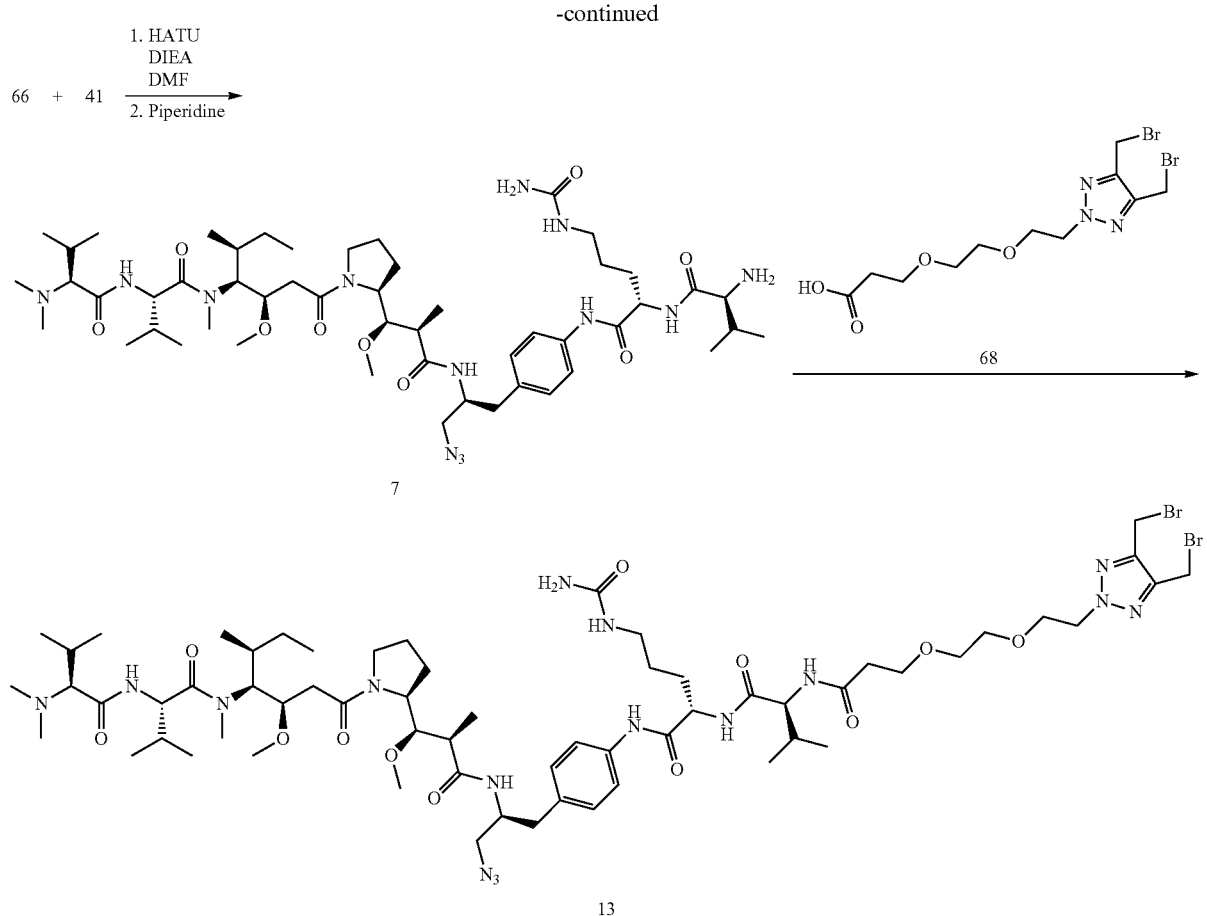

To compound 37 (130 mg, 0.26 mmol) in 3 mL of DMF was added HATU (110 mg, 0.29 mmol), DIEA (175 μL, 1 mmol), and amine 36 (110 mg, 0.27 mmol). The mixture was stirred for 30 min, then concentrated to dryness. The residue was then treated with TFA/DCM (1/4, v/v, 5 mL) for 30 min. The mixture was evaporated and purified by HPLC to give compound 66 (108 mg, 65%). MS m/z 670.5 (M+H).

To compound 41 (85 mg, 0.12 mmol) in 2 mL of DMF was added HATU (48 mg, 0.12 mmol), DIEA (83 μL, 0.48 mmol), and amine 66 (94 mg, 0.12 mmol). The mixture was stirred for 30 min, then piperidine (0.2 mL) was added and stirred for 30 min. The mixture was concentrated and purified by HPLC to give compound 67 (87 mg, 63%). MS m/z 1028.7 (M+H).

To a solution of compound 67 (57 mg, 0.05 mmol) and acid 68 (22 mg) in DCM/DMF (3/1, v/v, 4 mL) was added PyBrOP (0.055 mmol) and DIEA (35 μL). The mixture was stirred at room temperature for 30 min and then concentrated to about 2 mL. The residue was purified by reverse phase HPLC to give compound 13 (41 mg). MS m/z 1425.7 (M+H).

Example 9

This example provides the results of EC50 assays of the designated drug conjugated antibodies measured in vitro in specified cells. The antibody used was an anti-HER2 IgG class of antibody.

| Conjugate ID | SBKR3 (Her2+++) | HCC1954 (Her2+++) | SKOV-3 (Her2+++) | BT474 (Her2+++) | MDA-MB-453 (Her2++) | MDA-MB-175 (Her2+) | MDA-MB-361 (Her2+++) |
|---|---|---|---|---|---|---|---|
| | | | | EC50 [nM] | | | |
| 16 | 0.040 | 0.138 | 0.405 | 0.423 | 1.195 | 3.635 | |
| 17 | 0.106 | 0.237 | 0.334 | 0.623 | 26.42 | 20.08 | |
| 19 | 0.156 | 0.193 | 0.340 | 0.232 | 3.946 | | 0.640 |
| 21 | 0.3432 | 0.1788 | | 1.065 | | 0.4904 | 0.1326 |
| 22 | 0.06349 | 0.04926 | | 0.346 | 0.137 | 0.2628 | 0.04987 |
| 23 | 0.04644 | 0.03678 | | 0.345 | 0.118 | 0.2095 | 0.04657 |
| 65 | 0.158 | 0.117 | | 0.100 | 4.762 | | |

Example 10

This example shows in vivo efficacy of ADC 16 (an anti-Her2 antibody conjugate) in a Subcutaneous N87 Xenograft Model. FIG. 1 shows a single dose of conjugate 16 administered to BALB/c nude mice by intravenous administration. There were 8 mice in each group and total 6 groups of mice were studied: 3 groups were injected with T-DM1 (Trastuzumab—DM1 conjugate) at different doses; 2 groups were injected with ADC 16 at different doses; and one vehicle control. All the drugs were administered in the same manner (single dose). A single dose of ADC-16 iv. at 1 mg/kg or 3 mg/kg outperformed T-DM1 at 3 mg/kg or 10 mg/kg respectively. 3 mg/kg ADC-16 completely inhibited tumor growth up to 100 days.

Example 11

Figure 2:
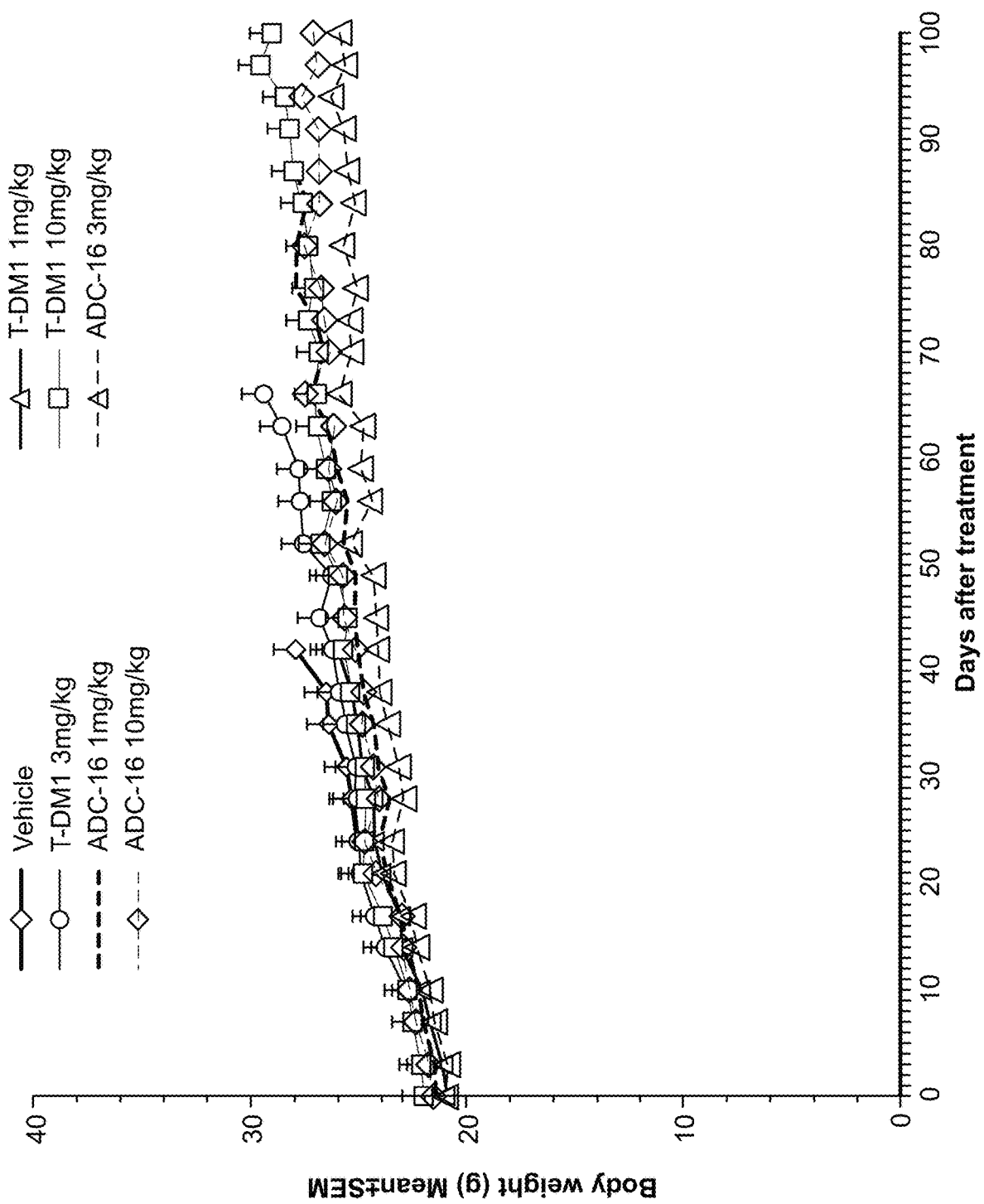
FIG. 2 shows a single dose of conjugate 15 administered to BALB/c nude mice (n=8) by intravenous administration.
Figure 3:
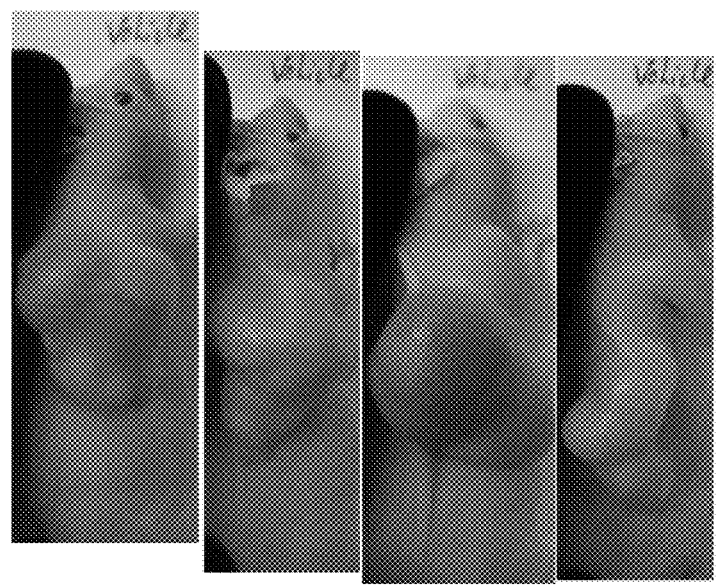
FIG. 3 shows pictures of the mice 35 days after treatment.
Figure 3:
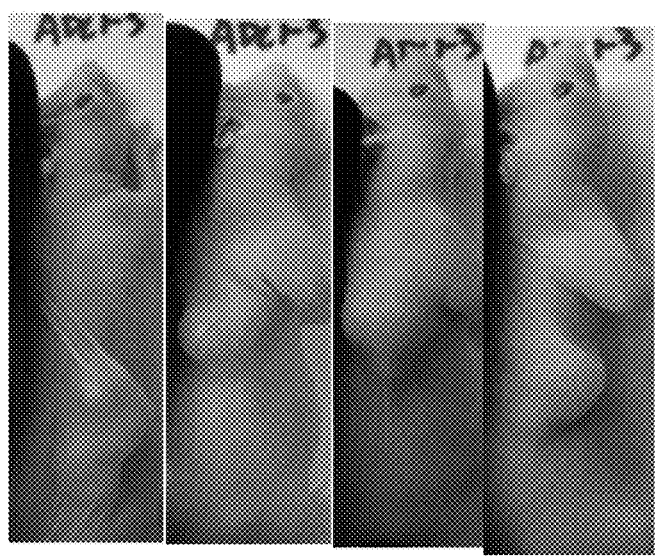
Figure 3:

This example shows in vivo safety of ADC 16 (an anti-Her2 antibody conjugate) in a Subcutaneous N87 Xenograft Model. FIG. 2 shows a single dose of conjugate 16 administered to BALB/c nude mice by intravenous administration. There were 8 mice in each group and total 7 groups of mice were studied: 3 groups were injected with T-DM1 (Trastuzumab—DM1 conjugate) at different doses; 3 groups were injected with ADC 16 at different doses; and one vehicle control. All the drugs were administered in the same manner (single dose). A single dose of ADC-16 iv. at 1 mg/kg, 3 mg/kg or 10 mg/kg did not retard body weight gain. The difference of the body weights between T-DM1 and ADC-16 groups were caused by the difference of tumor weight. FIG. 3 shows pictures of the mice 35 days after treatment.

Example 12

Figure 5:
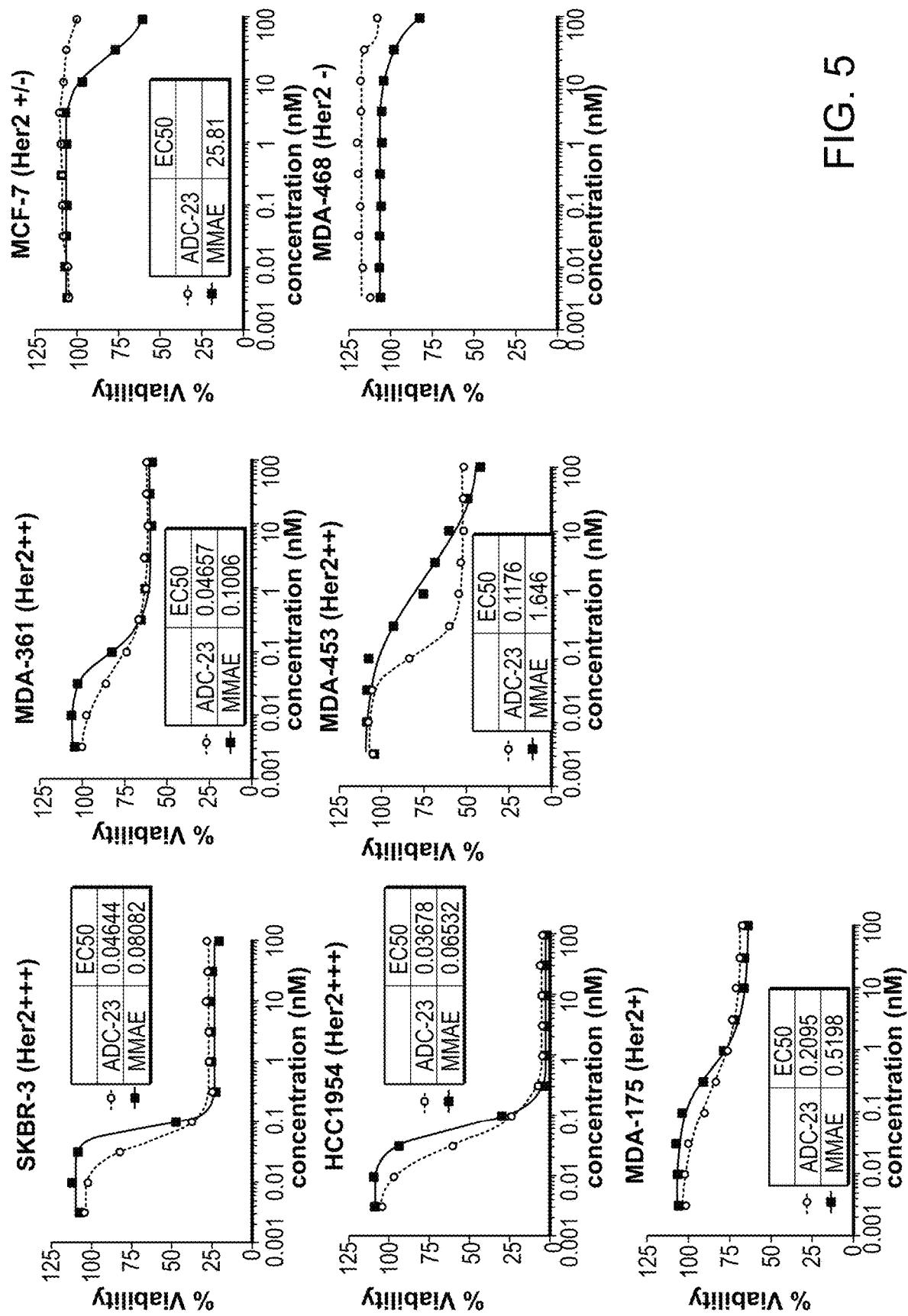
FIG. 5 shows in vitro activity of ADC-23 (anti-Her2 antibody) in a group of tumor cell lines.

This example (FIG. 5) shows ADC-23 induces equivalent or stronger anti-proliferative activity in breast cancer cell lines, compared to MMAE conjugates. In these studies, the cells were all treated with either ADC-23 or MMAE conjugates for 3 d. IC50 is determined as the concentration that showed 50% inhibition of cell growth.

Example 13

Figure 6:
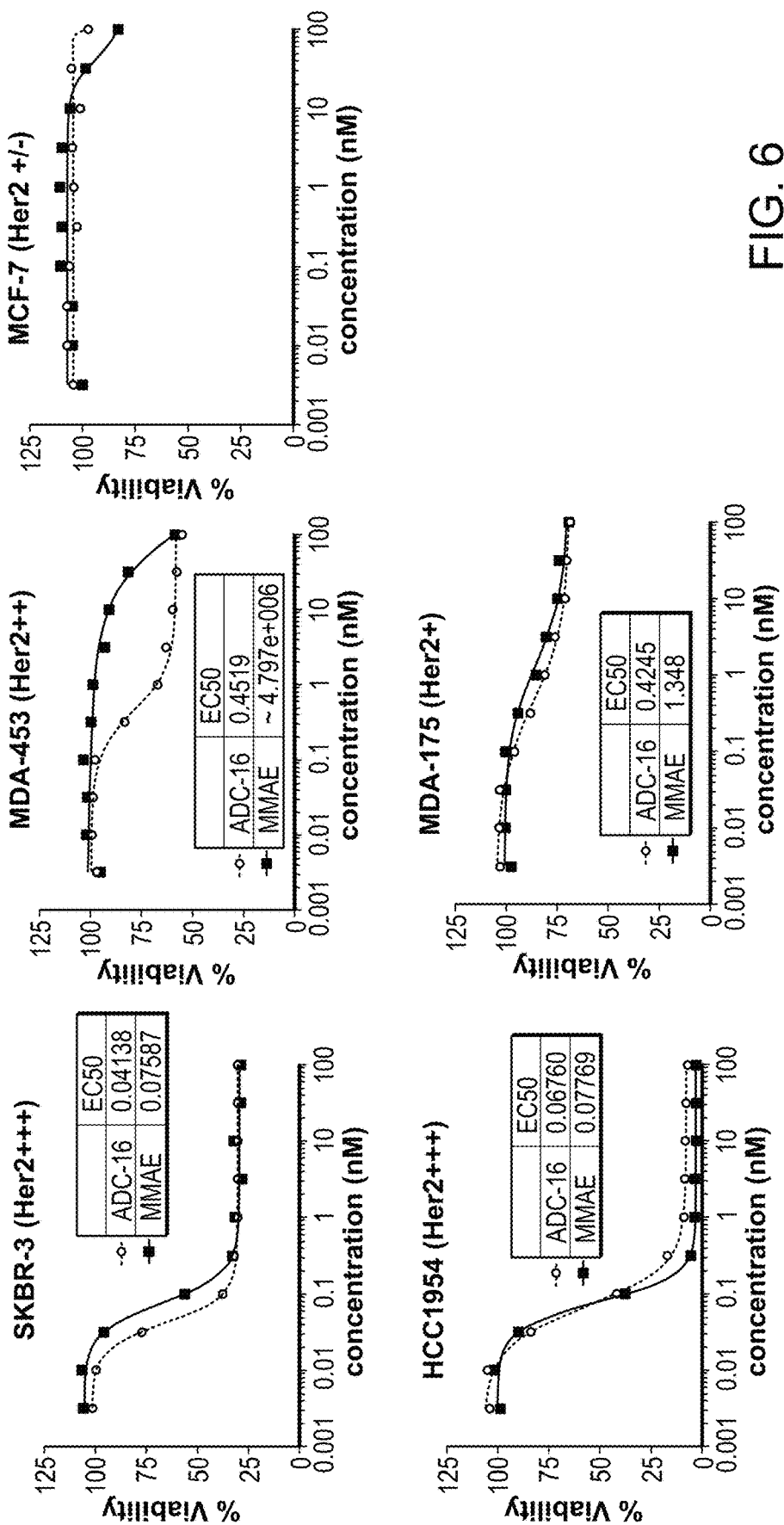
FIG. 6 shows in vitro activity of ADC-16 (anti-Her2 antibody) in a group of tumor cell lines.

This example (FIG. 6) shows ADC-16 induces equivalent or stronger anti-proliferative activity in breast cancer cell lines, compared to MMAE conjugates. In the above studies, the cells were all treated with either ADC-16 or MMAE conjugates for 3 d. IC50 is determined as the concentration that showed 50% inhibition of cell growth.

Example 14

Figure 7:
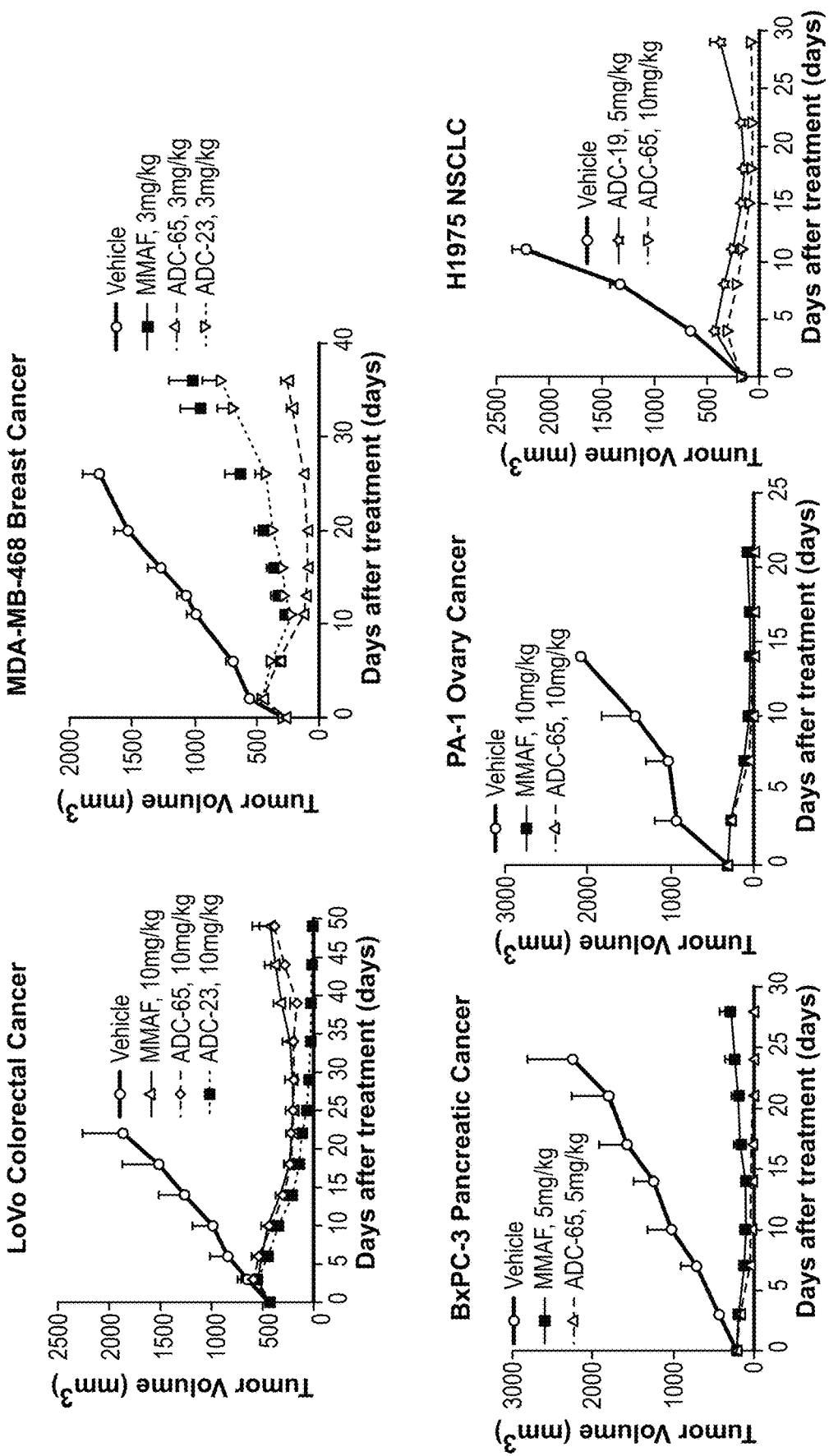
FIG. 7 shows in vivo efficacy of ADC-65, ADC-23 and ADC-19 in various xenograft tumor models.

This example (FIG. 7) shows the in vivo efficacy of ADC-65, ADC-23 and ADC-19 in LoVo (Colon), MDA-MB-468 (Breast), BxPC-3 (Pancreatic), PA-1 (Ovarian) and H1975 NSCLC xenograft nude mice. All ADCs were given as single dose via iv. at indicated concentrations. The ADCs tested outperformed MMAF in most cases at the same level, and completely inhibited tumor growth by single dose.

Example 15

Figure 4A:
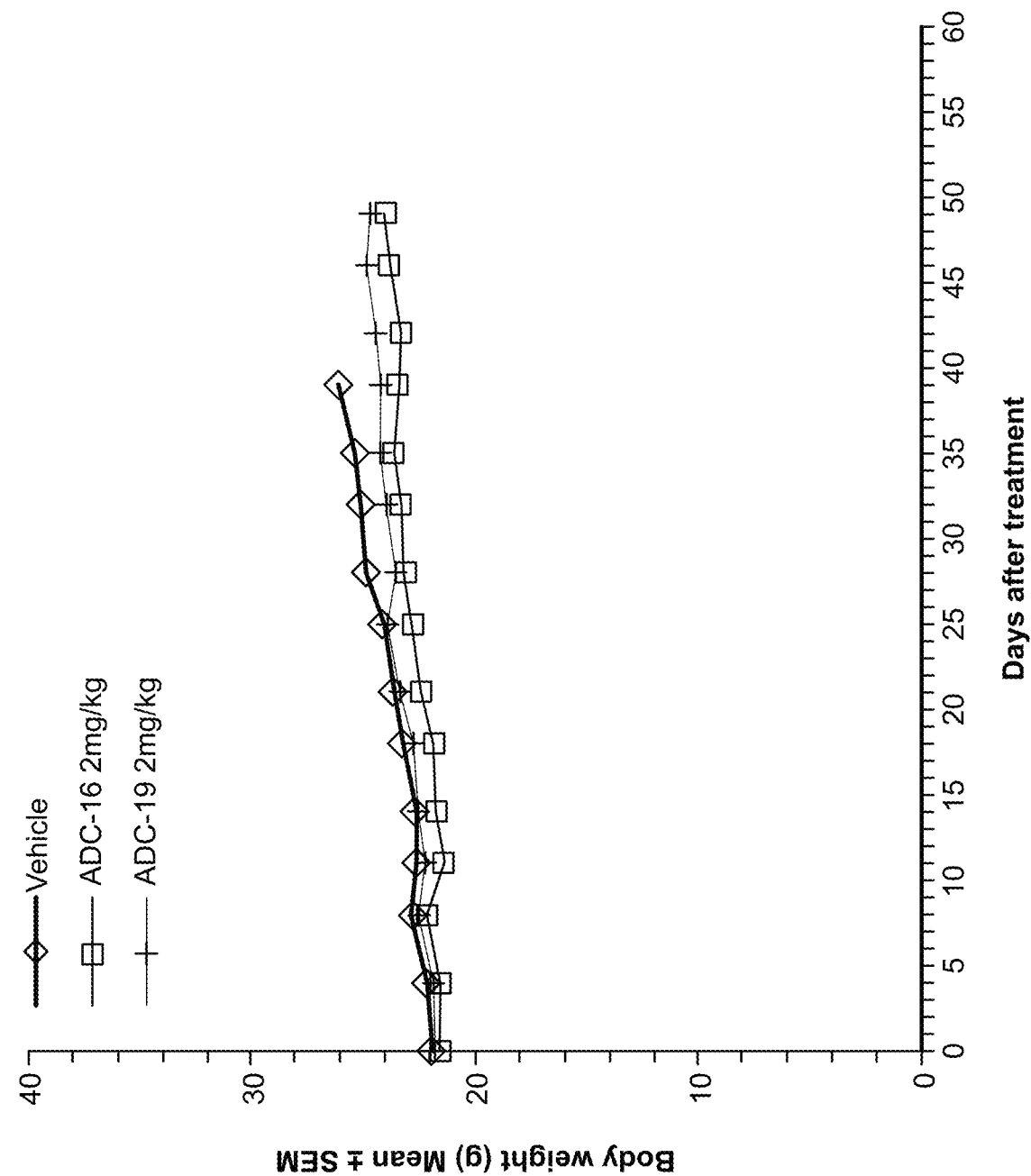
FIGS. 4A and 4B show a single dose of conjugates 16 and 19 administered to BALB/c nude mice (n=8) by intravenous administration.
Figure 4B:
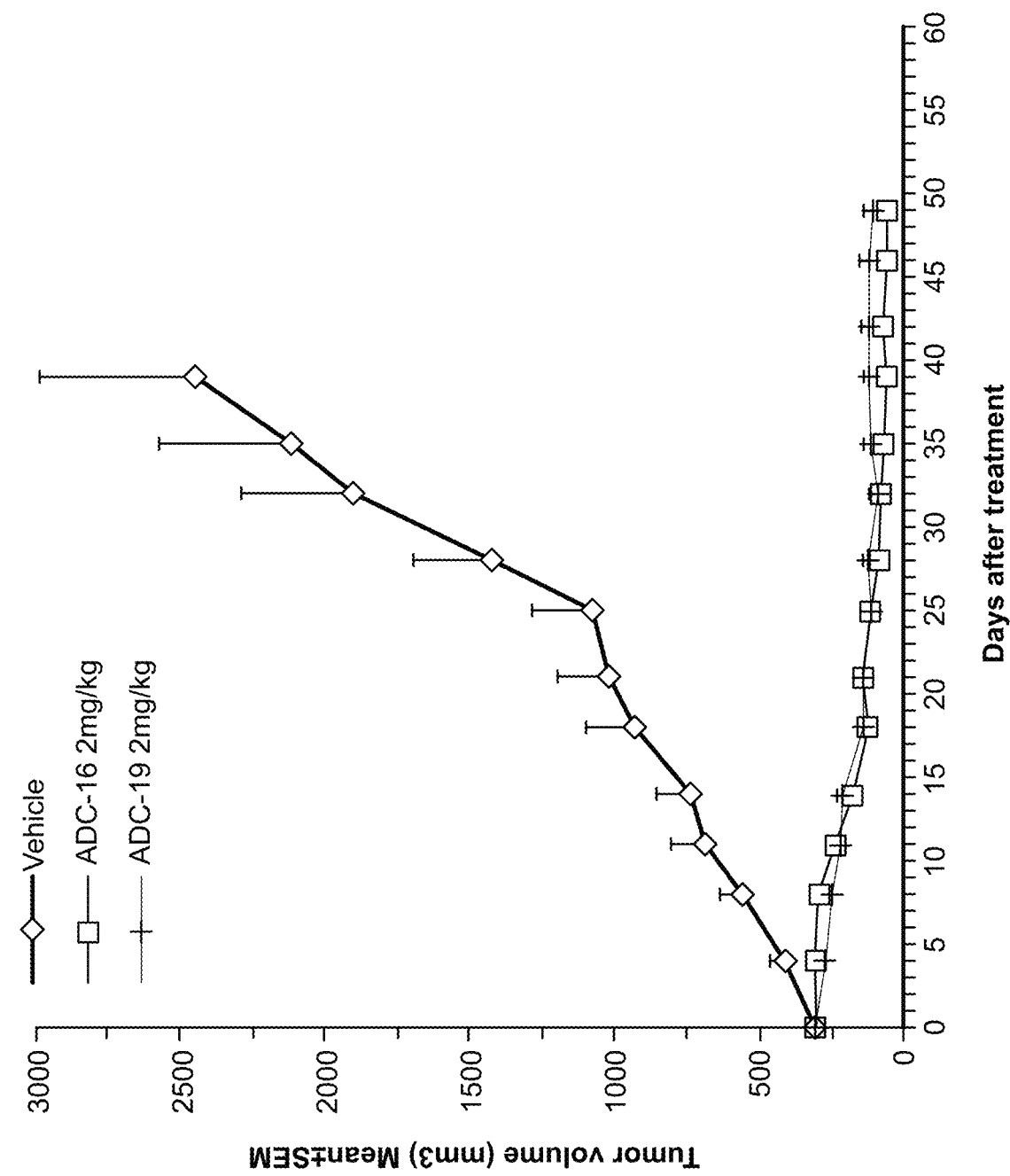

This example show in vivo safety and efficacy of ADC 19 (an anti-Her2 antibody conjugate) in a Subcutaneous N87 Xenograft Model. FIGS. 4A and 4B show a single dose of conjugate 19 administered to BALB/c nude mice by intravenous administration. There were 8 mice in each group and total 3 groups of mice were studied: 1 group of mice was injected with ADC 16; 1 group of mice was injected with ADC 19; and one vehicle control. All the drugs were administered in the same manner (single dose). A single dose of ADC-19 iv. at 2 mg/kg was comparable to that of ADC-16 at the same dose and completely inhibited tumor growth up to 49 days and did not retard body weight gain that was comparable to ADC-16.

Example 16

This example shows the general conjugation procedure for synthesizing antibody drug conjugates 16, 17, 19, and 64. To a solution of 0.5-50 mgs/mL of antibody in buffer at pH 6.0-9.0 with 0-30% organic solvent, was added 0.1-10 eq of activated drug linker conjugate (1, or 2, or 3, or 4, or 5, or 62) in a manner of portion wise or continuous flow. The reaction was performed at 0-40° C. for 0.5-50 hours with gentle stirring or shaking, monitored by HIC-HPLC. The resultant crude ADC product underwent necessary downstream steps of desalt, buffet changes/formulation, and optionally, purification, using the state-of-art procedures. The ADC product was characterized by HIC-HPLC, SEC, RP-HPLC, and optionally LC-MS.

Example 17

This example shows a general conjugation procedure for synthesizing antibody drug conjugates 21, 22, 23, 24, 28, and 65. To a solution of antibody, 0.5-50 mgs/mL, in a certain buffet at pH 5.0-9.0, such as PBS, was added 0.5-100 eq of reducing agent such as TCEP and DTT. The reduction was performed at 0-40° C. for 0.5-40 hours with gentle stirring or shaking, and then the reducing agent was removed by column or ultrafiltration. To the reduced antibody, 0.5-50 mgs/mL, in a certain buffet at pH 5.0-9.0, such as PBS, with 0-30% of organic co-solvent such as DMA, was added 0.5-10 eq of the drug-linker reactant (selected from compound 6-15, or 63). The reaction was conducted at 0-40° C. for 0.5-40 hours with gentle stirring or shaking, monitored by HIC-HPLC. The resultant crude ADC product underwent necessary down-stream steps of desalt, buffet changes/formulation, and optionally, purification, using the state-of-art procedures. The final ADC product was characterized by HIC-HPLC, SEC, RP-HPLC, and optionally LC-MS.

We claim:
1. A compound comprising Formula IV:

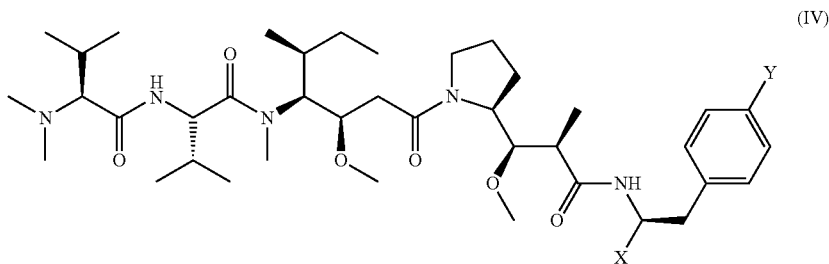

(IV)

wherein Y is OH or NH$_2$; and
X is —CH$_2$N$_3$.

2. An antibody drug-conjugate (ADC) comprising Formula I:

Ab-(-L$^1$-L$^2$-D)$_n$    (I)

or a pharmaceutically acceptable salt thereof,
wherein:
Ab is a monoclonal antibody;
L$^1$ is a connector;
L$^2$ is a linker comprising an amino acid, peptide, —(CH$_2$)$_n$—, —(CH$_2$CH$_2$O)$_n$—, —(C═O)—, -Val-Cit-, -Val-Ala-, -Ala-Ala-Asn-, -Ala-Val-Asn-, —(C═O)CH$_2$CH$_2$(C═O)—, —(C═O)CH$_2$CH$_2$O)—, —(CH$_2$CH$_2$O)$_n$—CH$_2$CH$_2$NH—, —(C═O)—CH$_2$—, or

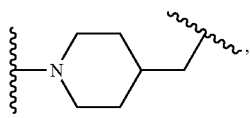, a combination thereof;
D is an active agent (Drug) having a structure of Formula II

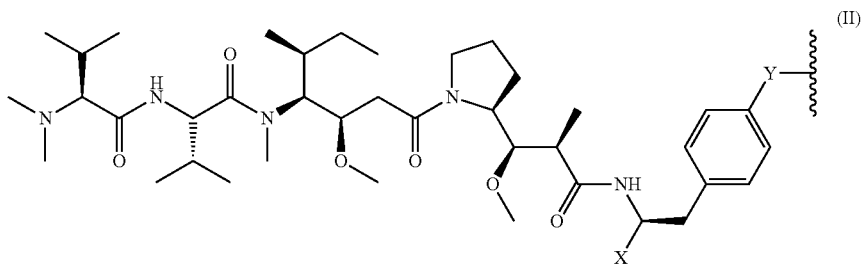

(II)

wherein Y is O or NH,
X is CH$_2$N$_3$; and
n is an integer from 1-8.

3. The ADC of claim 2, wherein the structure of Formula I has a structure selected from the group consisting of

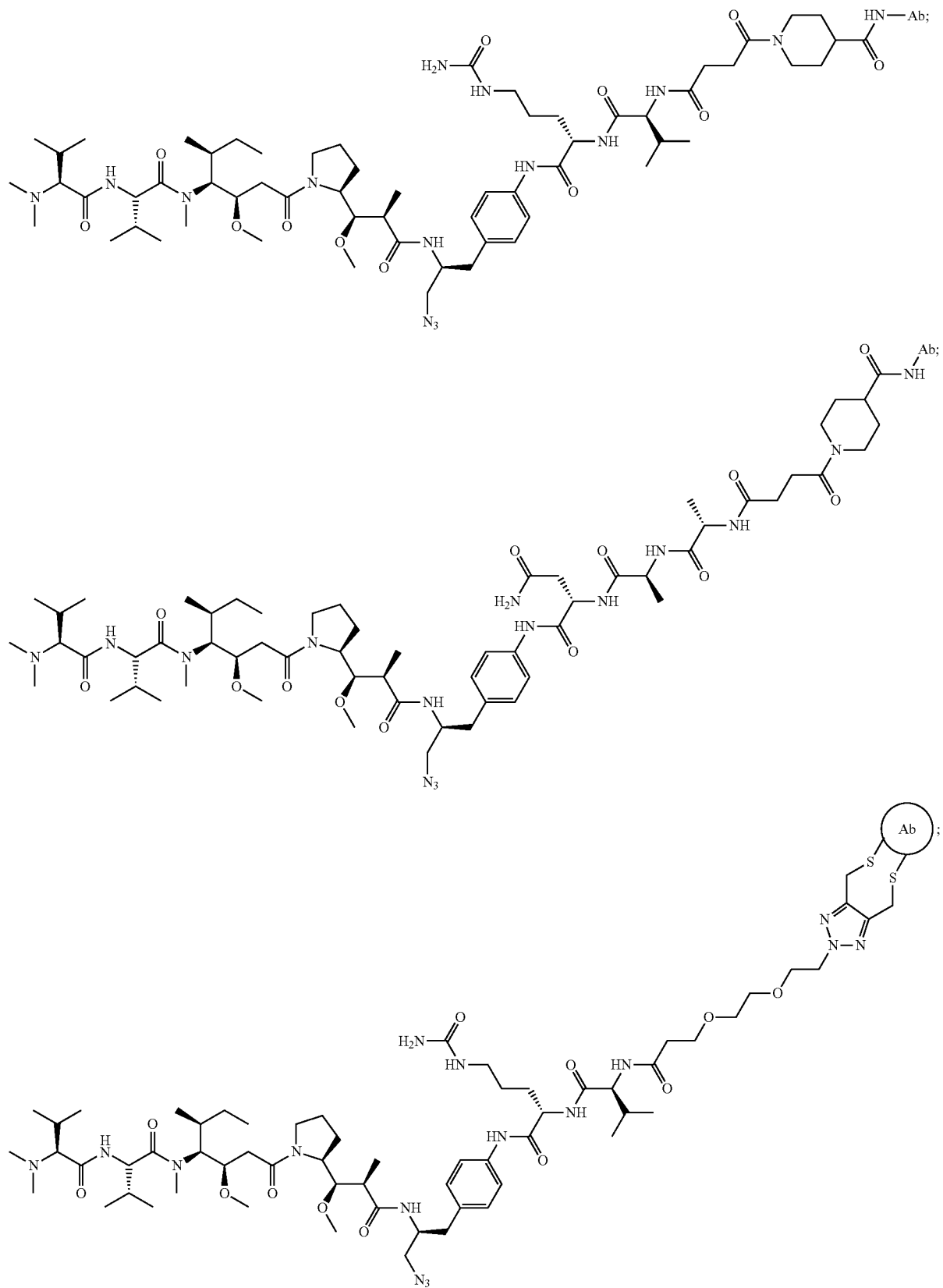
and

-continued

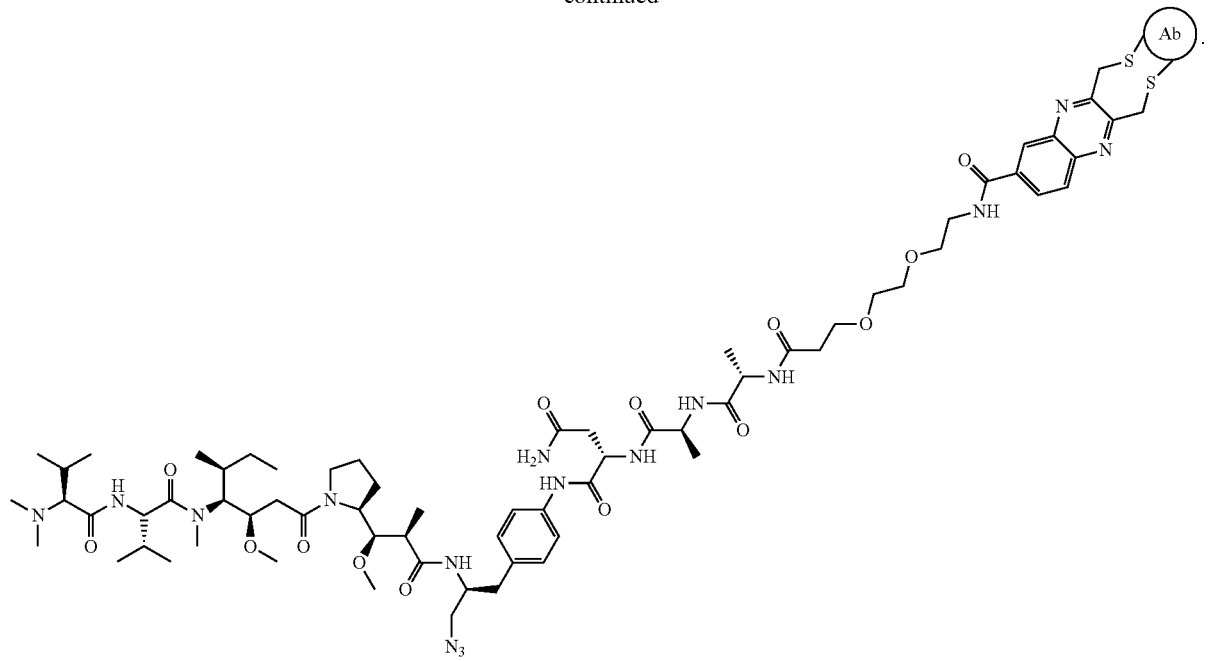

4. The ADC of claim 2, wherein L² is selected from the group consisting of —(C=O)—, —CH₂(C=O)—, -Cit-Val-(C=O)CH₂CH₂(C=O)—, -Asn-Ala-Ala-(C=O)CH₂CH₂(C=O)—, -Asn-Val-Ala-(C=O) CH₂CH₂(C=O)—, -Cit-Val-(C=O)CH₂CH₂OCH₂CH₂OCH₂CH₂—, -Cit-Val-(C=O)CH₂CH₂OCH₂CH₂OCH₂CH₂NH—, -Asn-Ala-Ala-(C=O)CH₂CH₂O(CH₂CH₂O)ₙCH₂CH₂NH(C=O)—,

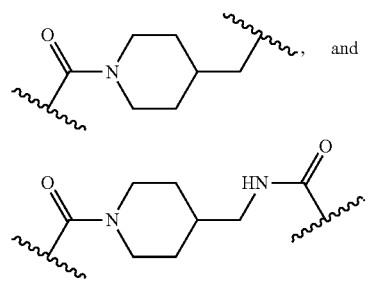
and

5. The compound of claim 1, wherein Y is OH.
6. The compound of claim 1, wherein Y is NH₂.
7. The ADC of claim 2, wherein L¹ comprises

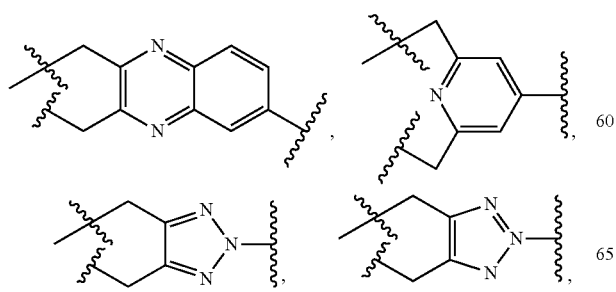

-continued

, or

8. The ADC of claim 2, wherein Y is NH.
9. The ADC of claim 2, wherein Y is O.
10. The ADC of claim 2, wherein -L¹-L², taken together with Ab, is selected from the group consisting of

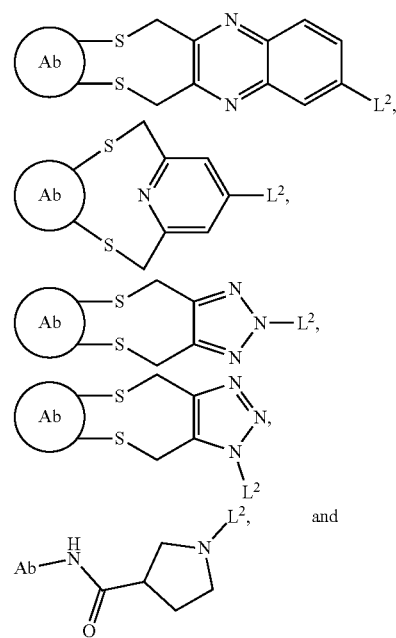

-continued
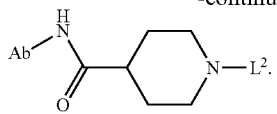
11. The ADC of claim 2, wherein $L^1$ comprises
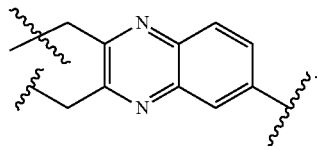 [SMILES: *Cc1nc2ccc(*)cc2nc1C*]
12. The ADC of claim 2, wherein $L^1$ comprises
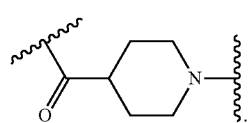 [SMILES: *C(=O)C1CCN(*)CC1]
13. The ADC of claim 2, wherein -$L^1$-$L^2$, taken together with Ab, is
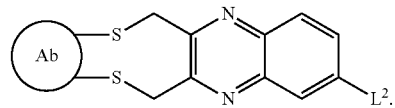
14. The ADC of claim 2, wherein -$L^1$-$L^2$, taken together with Ab, is
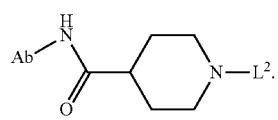
* * * * *